United States Patent
Zvuloni et al.

(10) Patent No.: US 9,561,346 B2
(45) Date of Patent: Feb. 7, 2017

(54) CATHETERIZATION APPARATUS AND METHODS THEREOF

(71) Applicant: UC-CARE LTD., Yokneam (IL)

(72) Inventors: Roni Zvuloni, Haifa (IL); Shaike Schatzberger, Haifa (IL)

(73) Assignee: UC-CARE LTD., Yokneam (IL)

( * ) Notice: Subject to any disclaimer, the term of this patent is extended or adjusted under 35 U.S.C. 154(b) by 143 days.

(21) Appl. No.: 14/371,208

(22) PCT Filed: Jan. 10, 2013

(86) PCT No.: PCT/IL2013/050024
§ 371 (c)(1),
(2) Date: Jul. 9, 2014

(87) PCT Pub. No.: WO2013/105091
PCT Pub. Date: Jul. 18, 2013

(65) Prior Publication Data
US 2015/0018802 A1    Jan. 15, 2015

Related U.S. Application Data

(60) Provisional application No. 61/585,262, filed on Jan. 11, 2012.

(51) Int. Cl.
*A61M 31/00*    (2006.01)
*A61M 25/01*    (2006.01)
(Continued)

(52) U.S. Cl.
CPC ........ *A61M 25/0102* (2013.01); *A61B 18/02* (2013.01); *A61M 25/008* (2013.01);
(Continued)

(58) Field of Classification Search
CPC ............... A61M 25/0102; A61M 25/0017;
A61M 25/0074; A61M 25/0075; A61M 25/008; A61M 25/1025; A61M 25/0026–25/003; A61M 25/0067; A61M 25/0068; A61M 25/0039; A61M 2025/0004; A61M 2025/0175; A61M 2025/0681; A61M 2025/0076; A61M 2025/0078; A61M 2210/1085; A61M 2210/1089; A61M 2210/1078; A61M 2210/1096; A61B 12/02; A61B 12/0206; A61B 2018/0212; A61B 2018/00047; A61B 2018/00547; A61B 2018/0262; A61B 2018/00517
(Continued)

(56) References Cited

U.S. PATENT DOCUMENTS 4,740,195 A * 4/1988 Lanciano .......... A61M 25/0017
600/434
5,261,416 A * 11/1993 Taussig ............ A61B 10/0045
600/572
(Continued)

FOREIGN PATENT DOCUMENTS

WO    2007/041695    4/2007
WO    2010003135     1/2010

OTHER PUBLICATIONS

Stensballe et al., (2005) Hydrophilic-coated catheters for intermittent catheterisation reduce urethral micro trauma: a prospective, randomised, participant-blinded, crossover study of three different types of catheters. Eur Urol 48(6): 978-83.
(Continued)

*Primary Examiner* — Edelmira Bosques
*Assistant Examiner* — Leah Swanson
(74) *Attorney, Agent, or Firm* — Dorsey & Whitney LLP

(57) ABSTRACT

A containing catheter for facilitating sequential treatment operations therethrough, is provided. The containing catheter comprises a median portion comprising an elongated,
(Continued)

substantially tubular member, and a distal portion, comprising a distal stiff member. A catheterization apparatus is provided, comprising the containing catheter and an elongated inner catheter insertable into the containing catheter. A method of catheterization is provided, comprising providing the containing catheter, stiffening a portion of the containing catheter and inserting the stiffened containing catheter into a body conduit of a patient.

18 Claims, 9 Drawing Sheets

(51) Int. Cl.
  *A61M 25/00*  (2006.01)
  *A61M 25/10*  (2013.01)
  *A61B 18/02*  (2006.01)
  *A61B 18/04*  (2006.01)
  *A61B 18/00*  (2006.01)
  *A61M 25/06*  (2006.01)

(52) U.S. Cl.
  CPC .... *A61M 25/0017* (2013.01); *A61M 25/0075* (2013.01); *A61M 25/1025* (2013.01); *A61B 2018/00041* (2013.01); *A61B 2018/00517* (2013.01); *A61B 2018/00547* (2013.01); *A61B 2018/0212* (2013.01); *A61B 2018/0262* (2013.01); *A61B 2018/046* (2013.01); *A61M 25/0041* (2013.01); *A61M 2025/0004* (2013.01); *A61M 2025/0047* (2013.01); *A61M 2025/0175* (2013.01); *A61M 2025/0681* (2013.01); *A61M 2210/1085* (2013.01); *A61M 2210/1089* (2013.01)

(58) Field of Classification Search
  USPC .......................................................... 604/517
  See application file for complete search history.

(56) References Cited

U.S. PATENT DOCUMENTS

| | | | |
|---|---|---|---|
| 5,489,269 | A | 2/1996 | Aldrich |
| 6,096,013 | A | 8/2000 | Hakky |
| 6,159,195 | A * | 12/2000 | Ha .................... A61M 25/0068 |
| | | | 604/103.04 |
| 7,670,333 | B2 | 3/2010 | Schatzberger |
| 2002/0165521 | A1 | 11/2002 | Cioanta |
| 2004/0186538 | A1 | 9/2004 | Eshel |
| 2009/0118724 | A1 | 5/2009 | Zvuloni |
| 2009/0247987 | A1 | 10/2009 | Chevalier, Jr. |
| 2009/0299358 | A1 * | 12/2009 | Lafontaine ............. A61B 18/02 |
| | | | 606/21 |
| 2010/0268159 | A1 * | 10/2010 | Engel .................... A61L 29/126 |
| | | | 604/99.03 |

OTHER PUBLICATIONS

Vapnek et al., (2003) A prospective randomized trial of the LoFric hydrophilic coated catheter versus conventional plastic catheter for clean intermittent catheterization. J Urol 169(3): 994-8.

* cited by examiner

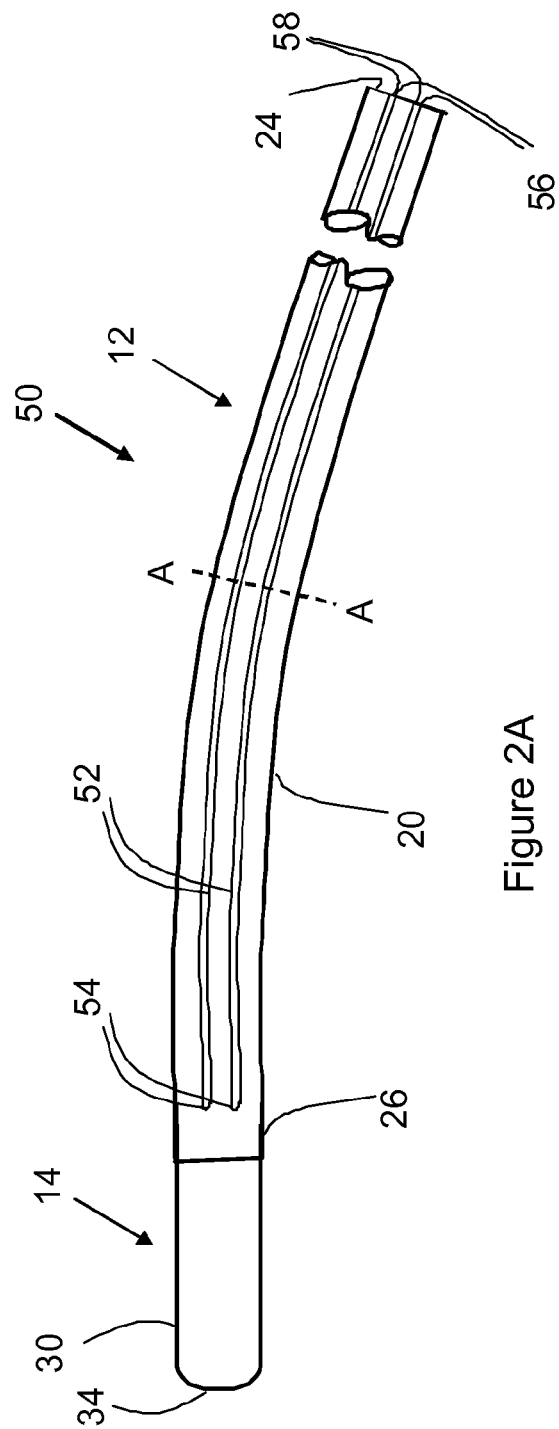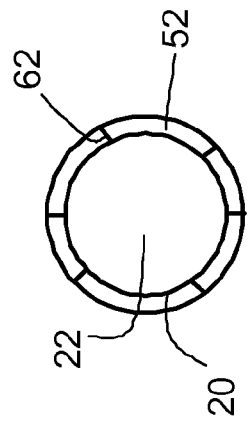

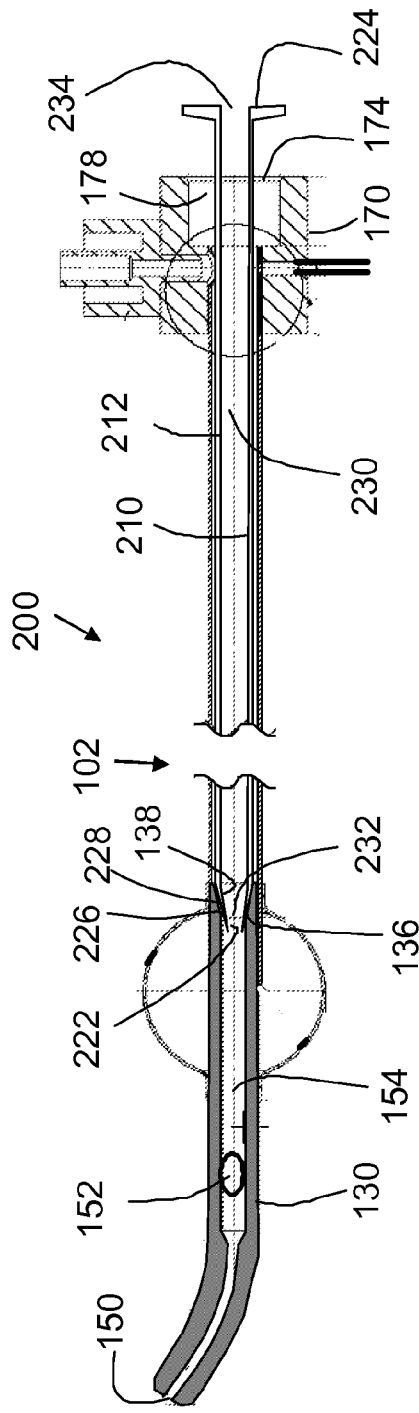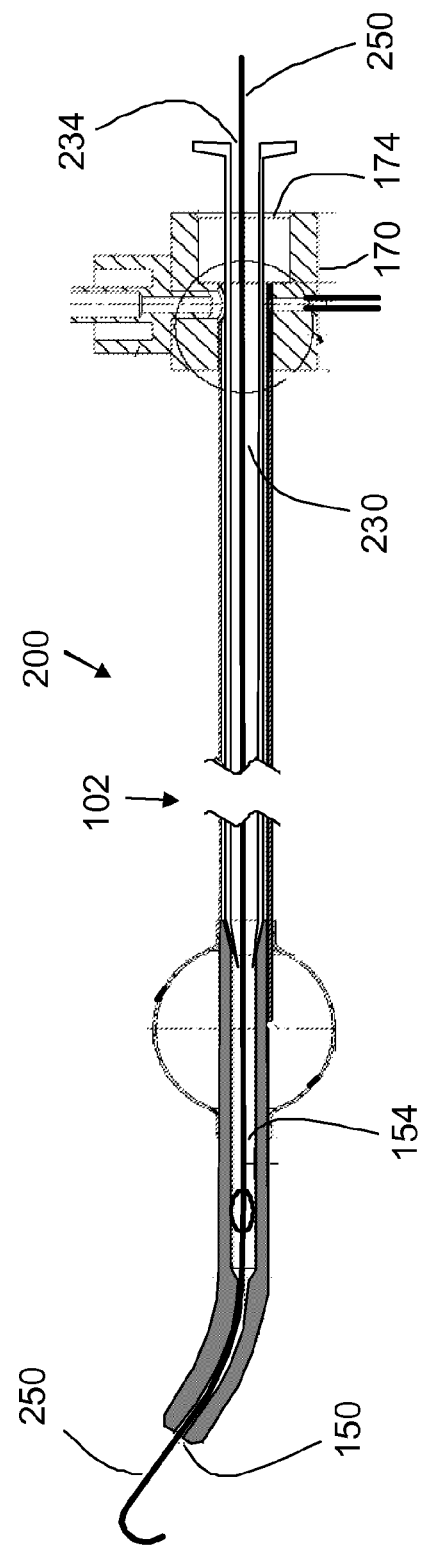

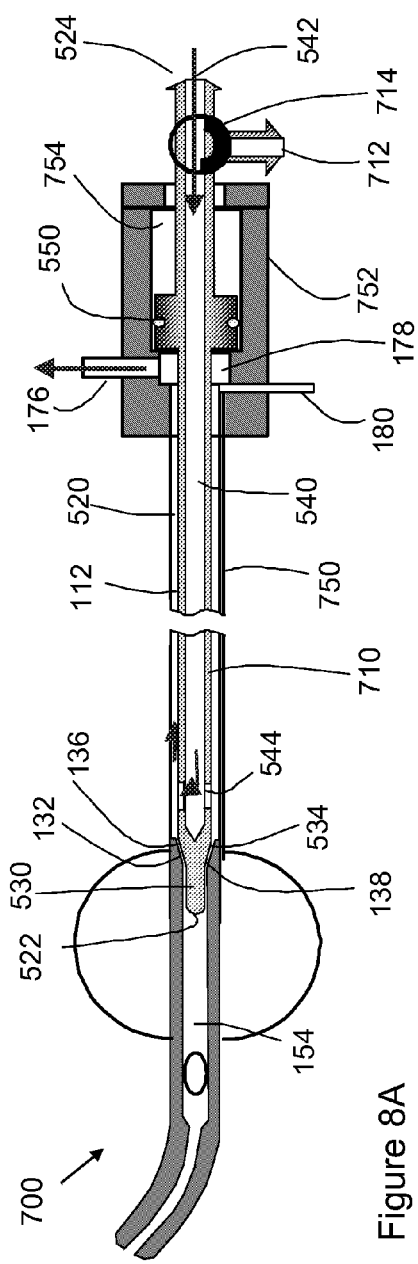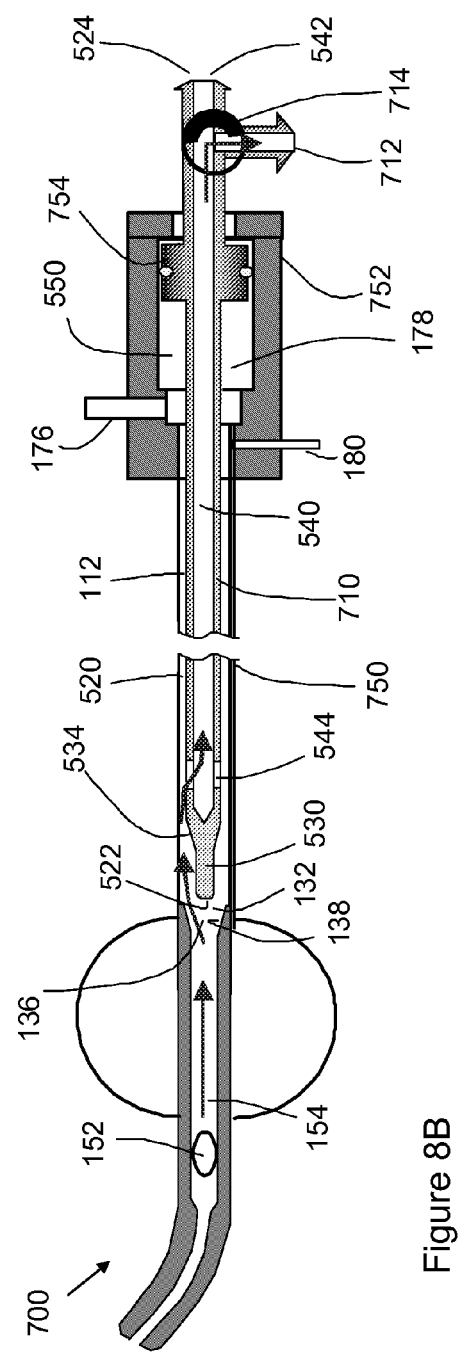
Figure 8A
Figure 8B

CATHETERIZATION APPARATUS AND METHODS THEREOF

FIELD OF THE INVENTION

The invention, in some embodiments, relates to the field of catheters and more particularly, but not exclusively, to a containing catheter and a catheterization apparatus that in some embodiments are superior to catheters known in the art.

BACKGROUND OF THE INVENTION

Known medical procedures that employ catheterization, typically involve use of a plurality of catheters in sequence. Specifically, several catheters may be inserted into a same body conduit and removed from it, sequentially, to perform a sequence of steps of a medical procedure. To take an example, in cryosurgical ablation of prostate tissue, a procedure may typically involve a step of insertion of a guiding catheter into the urethra for identifying the urethral course during ultrasound-guided needle insertion. A next step may involve removal of the guiding catheter and insertion into the urethra of a treatment catheter. Such a treatment catheter may be for example a warming catheter used to protect the urethra during cryoablation, or, as another example, a urethral straightener connected to a probe guidance mechanism as taught by Zvuloni et al. in U.S. Pat. No. 7,670,333 and in Patent Application US20090118724. A next step may involve removal of the treatment catheter and insertion of a post-procedure drainage catheter. Finally, the drainage catheter must also be removed. Various other well-known treatment procedures similarly require two or three or more sequential catheter insertions and removals.

SUMMARY OF THE INVENTION

As discussed above, prior art procedures for catheterization involve sequential insertion and removal of catheters from a body conduit during a single procedural operation. Typically, each catheter in the sequence is designed to serve a specific goal, facilitating a specific step or only a few specific steps in the process of the operation.

Repeated sequential insertion and removal of a series of catheters can cause trauma to the body conduit along the trajectory of insertion, and increase risk of infection. Coating a urethral catheter by a hydrophilic coating may reduce friction and reduce micro-trauma to the body conduit; for instance, J. Stensballe, et al ("Hydrophilic-Coated Catheters for Intermittent Catheterisation Reduce Urethral Micro Trauma: A Prospective, Randomised, Participant-Blinded, Crossover Study of Three Different Types of Catheters", European Urology, Vol 48 (6), (2005) P. 978-983), and J. M. Vapnek et. al. ("A prospective randomized trial of the LoFric hydrophilic coated catheter versus conventional plastic catheter for clean intermittent catheterization.", J Urol. March; 169(3)(2003) P. 994-998) show that employing hydrophilic coating to a urethral catheter may reduce risk of trauma and infection to the urethra. However, such hydrophilic coating is not sufficient to eliminate these risks completely.

Moreover, each insertion and removal of a catheter from a body conduit adds to the complexity and to the duration of the operation. Increased complexity and duration of an operation increase in turn overall risk and discomfort to the patient, decrease utilization efficiency of related medical infrastructure and adds to the operation costs, increasing thereby the overall financial load associated with the related medical procedure.

According to an aspect of some embodiments, there is thus provided a containing catheter insertable to body conduit for facilitating sequential treatment operations therethrough. The containing catheter comprises a median portion comprising an elongated, substantially tubular member, having a main lumen therein extending between a proximal end and a distal end of the tubular member. The main lumen thus provides fluid communication between the proximal end and the distal end of the tubular member. The containing catheter further comprises a distal portion, comprising a distal stiff member extending between a stiff member proximal end and a stiff member distal end. The distal stiff member comprises:

a proximal opening located at the distal stiff member's proximal end, and comprising a mating surface of a sealed joint;
a distal opening, and
a stiff member void inside the distal stiff member, configured to provide fluid communication between the proximal opening and the distal opening.

The distal portion is physically associated with the median portion so that the stiff member void of the distal stiff member is in fluid communication with the main lumen.

As used herein, two points, or regions, are said to have fluid communication between them if they are connected by a substantially confined and continuous void so that fluid may flow from one point or region to the other point or region.

According to an aspect of some embodiments, the containing catheter may be used to facilitate and simplify various medical procedures that require sequential insertion and removal of catheters or other components or instrumentations into a body conduit. According to an aspect of some embodiments, the containing catheter is inserted into the body conduit and then other catheters, components and instrumentations, required for various steps of the medical procedure, are sequentially inserted into the containing catheter and removed therefrom. The containing catheter prevents direct contact and friction between the body conduit and the other catheters or components or instrumentations inserted therein, and thereby significantly contributes to reducing risk of trauma or infection to the body conduit, that could otherwise occur. Further, inserting such other catheters or components into the containing catheter is much easier than inserting the same directly into the body conduit. Thus the overall duration of a medical procedure that involves sequential insertion of several catheters and components into the body conduit, may significantly be reduced.

According to some embodiments the tubular member of the containing catheter is soft. In some embodiments the median portion of the containing catheter is configured to be stiffened to enable insertion of the containing catheter through a body conduit.

By soft tubular member it is meant that the tubular member may easily fold and wrinkle when subject to a weak force or low pressure. Particularly, the tubular member may fold or wrinkle when it is attempted to insert the containing catheter into a body conduit. Thus a containing catheter comprising a soft tubular member may be inserted into a body conduit only if the tubular member is stiffened. By stiff member it is meant that such stiff member may flex, but may not fold or wrinkle when subject to a weak force or a low pressure. Particularly, a stiff member may be inserted into a body conduit e.g. by suitably pushing the member's proximal portion, so that the stiff member does not fold or wrinkle under the friction force associated with such insertion. By a flexible member it is meant that the flexible member may flex when subject to forces applied during employment of methods described herein, and the member returns to its original shape when such flexing forces are removed. By a rigid member it is meant that the rigid member does not substantially flex or break when subject to forces applied during employment of methods described herein.

According to an aspect of some embodiments there is provided a method of catheterization, comprising: providing the containing catheter with the soft tubular member described above; stiffening the median portion of the containing catheter, and inserting the stiffened containing catheter into a body conduit of a patient.

According to an aspect of some embodiments there is provided a catheterization apparatus comprising the containing catheter described above and an elongated inner catheter insertable into the main lumen of the containing catheter. The inner catheter extends between an inner catheter proximal end and an inner catheter distal end, having a length greater than a length of the median portion of the containing catheter.

According to some embodiments the inner catheter comprises a stiff and flexible portion, enabling to stiffen the tubular member when the inner catheter is inserted into the containing catheter and allowing inserting the stiffened containing catheter into a body conduit.

According to some embodiments the inner catheter distal end comprises an inner catheter mating surface configured to fit the mating surface of the proximal opening at the stiff member proximal end. The inner catheter mating surface and the mating surface of the distal stiff member form a sealing joint when the inner catheter is inserted into the containing catheter and pressed onto the distal stiff member.

According to some embodiments the inner catheter distal end is blind thereby preventing fluid flow through the proximal opening of the distal stiff member when the inner catheter is inserted into the containing catheter and pressed onto the distal stiff member.

According to some embodiments the inner catheter is hollow, having an inner catheter channel between a proximal catheter opening and a distal catheter opening.

According to some embodiments the distal catheter opening is at the inner catheter distal end. When the inner catheter is inserted into the containing catheter and pressed onto the distal stiff member a sealing joint is formed, allowing fluid communication between the inner catheter channel and the stiff member void.

According to some embodiments the inner catheter has a cross-section dimension smaller than a cross-section dimension of the main lumen, thereby forming a gap between the inner catheter and an inner surface of the tubular member, when the inner catheter is inserted into the containing catheter.

According to some embodiments the inner catheter distal end is blind, and the distal catheter opening is proximal to the inner catheter distal end and facing the gap between the inner catheter and the inner surface of the tubular member. When the inner catheter is inserted into the containing catheter and pressed onto the distal stiff member, fluid communication is thereby provided between the inner catheter channel and the gap, through the inner catheter distal opening.

According to some embodiments the catheterization apparatus is operable in at least two operational states according an arrangement of the inner catheter inside the containing catheter, wherein:

in a first operational state the inner catheter is inserted into the containing catheter and advanced until the inner catheter distal end is pressed onto the mating surface of the proximal opening of the distal stiff member, so that fluid flow through the proximal opening of the distal stiff member is prevented. A fluid forced into the inner catheter channel flows towards the inner catheter distal end inside the inner catheter channel, exits the inner catheter hollow channel through the distal catheter opening, and flows in the gap inside the main lumen towards the proximal end, while fluid flow through the proximal opening of the distal stiff member is prevented, and in a second operational state the inner catheter is retreated inside the containing catheter so that the inner catheter distal end disengages from the mating surface of the proximal opening of the distal stiff member, thereby allowing fluid communication between the stiff member void and the main lumen of the containing catheter through the proximal opening.

According to some embodiments the inner catheter comprises a rigid pole insertable into the containing catheter, and extends between the inner catheter distal end to a length greater than a length of the median portion of the containing catheter.

According to some embodiments the catheterization apparatus further comprises:
 a mechanical arm mechanically attached to the inner catheter proximal to the inner catheter proximal end; and
 a positioning template mechanically attached to the mechanical arm and configured to fixedly attach to a treatment tool.

According to some embodiments, position and orientation of the positioning template relative to the rigid pole can be established by a user by controllably modifying at least one of the mechanical attachments, thereby allowing aiming a treatment tool attached to the positioning template to a treatment locus having a known spatial relationship with the rigid pole.

Aspects and embodiments of the invention are described in the specification hereinbelow and in the appended claims.

Unless otherwise defined "about" herein means±10%. Unless otherwise defined, all technical and scientific terms used herein have the same meaning as commonly understood by one of ordinary skill in the art to which this invention pertains. In case of conflict, the patent specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 2A and 2B schematically depict an embodiment of a containing catheter comprising stiffening lumens;

FIG. 2C schematically depicts an embodiment of a containing catheter comprising a single stiffening lumen;

FIGS. 4A and 4B schematically depict an embodiment of a catheterization apparatus comprising the containing catheter of FIG. 3, and an embodiment of an introducer inner catheter;

DESCRIPTION OF SOME EMBODIMENTS OF THE INVENTION

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Figure 1A:
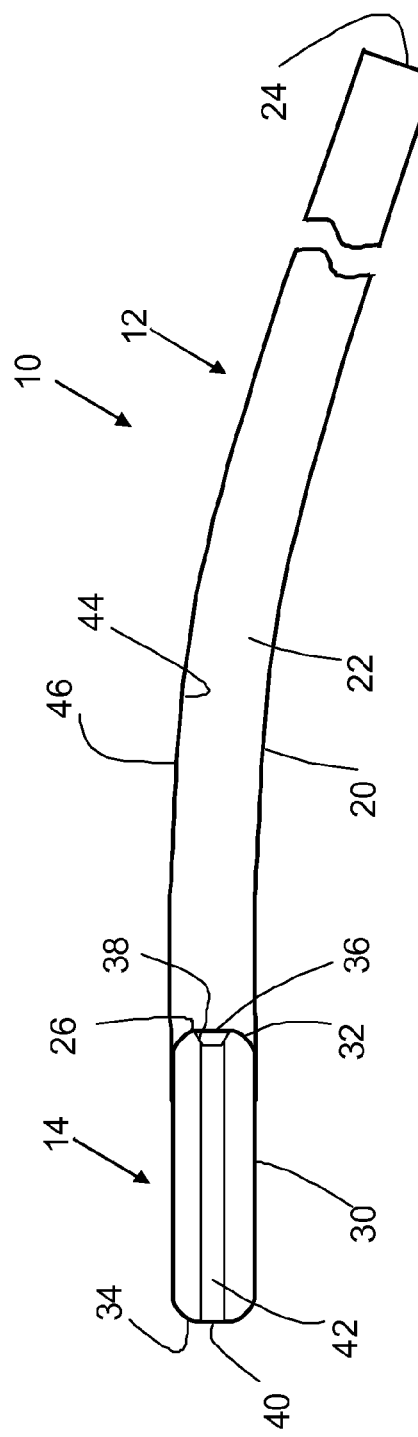
FIG. 1A schematically depicts a cross sectional view of an embodiment of a containing catheter as described herein.

An embodiment of a containing catheter 10 as described herein, is schematically depicted in cross-section in FIG. 1A. Containing catheter 10 comprises a median portion 12 and a distal portion 14. Median portion 12 comprises an elongated, tubular member 20. Tubular member 20 comprises a main lumen 22 extending between a proximal end 24 and a distal end 26 of tubular member 20, providing fluid communication between proximal end 24 and distal end 26.

Distal portion 14 comprises a distal stiff member 30 extending between a stiff member proximal end 32 and a stiff member distal end 34. According to some embodiments distal stiff member 30 is flexible enough to flex during insertion of containing catheter 10 into a body conduit, to conform to size and track of the body conduit along the insertion path. According to some embodiments, distal stiff member 30 is made of flexible plastics. According to some embodiments, distal stiff member 30 is made substantially of latex. According to some embodiments, distal stiff member 30 is made substantially of hard latex. According to some embodiments, distal stiff member 30 is made substantially of silicone.

Distal stiff member 30 comprises a proximal opening 36 located at stiff member proximal end 32, and comprising a mating surface 38 of a sealed joint. Stiff member 30 further comprises a distal opening 40 and a stiff member void 42. Stiff member void 42 is configured to provide fluid communication between proximal opening 36 and distal opening 40.

Distal end 26 of tubular member 20 is attached to stiff member 30 near stiff member proximal end 32, thereby physically associating proximal portion 12 with distal portion 14 so that stiff member void 42 of distal stiff member 30 is in fluid communication with main lumen 22. In some embodiments tubular member 20 is soft. In some embodiments tubular member 20 is made of biocompatible soft plastics (e.g. polyether block amide such as Pebax® by Arkema). In embodiments wherein median portion 12 is soft, median portion 12 is configured to be stiffened to enable insertion of containing catheter 10 through a body conduit, substantially by stiffening tubular member 20, as is further explained and detailed below.

According to some embodiments, containing catheter 10 is configured to contain an insertable member, for example an inner catheter, which is inserted into main lumen 22 of containing catheter 10. According to some embodiments, containing catheter 10 comprises a biocompatible lubricant coated on an inner surface 44 of tubular member 20, thereby reducing friction between inner surface 44 and an insertable member (not shown) inserted therein. According to some embodiments such biocompatible lubricant comprises a hydrophilic material. According to some embodiments containing catheter 10 comprises a biocompatible hydrophilic material layer coated on an outer surface 46 of containing catheter 10, to reduce friction between containing catheter 10 and a body conduit when containing catheter 10 is inserted into the body conduit. According to some embodiments such biocompatible hydrophilic layer is coated on outer surface 46 along tubular member 20. According to some embodiments such biocompatible hydrophilic layer is coated on outer surface 46 along distal stiff member 30.

FIG. 2A schematically depicts a containing catheter 50 according to some embodiments, and FIG. 2B schematically depicts containing catheter 50 in cross-section view AA. Containing catheter 50 is different from containing catheter 10 in that median portion 12 of containing catheter 50 comprises stiffening lumens 52, extending along tubular member 20. Each stiffening lumen 52 is extending between a stiffening lumen distal end 54 and a stiffening lumen proximal end 56. Stiffening lumen distal end 54 is closed, and stiffening lumen proximal end 56 is open, providing a stiffening lumen opening 58 to each stiffening lumen 52. By pressurizing a fluid into each stiffening lumen 52 through a respective stiffening lumen opening 58, tubular member 20, and hence median portion 12 may be stiffened.

Embodiments of containing catheter 50 may comprise one or two or a plurality of stiffening lumens arranged along median portion 12 of containing catheter 50. FIGS. 2B and 2C schematically depict two examples in a non-limiting manner and other arrangements are contemplated. FIG. 2B schematically depicts an embodiment wherein five stiffening lumens are arranged circumferentially around the circumference of tubular member 50. FIG. 2C schematically depicts an embodiment wherein a single stiffening lumen 52, having a ring shape in a cross-section view, encompasses tubular member 20, whereas short septa 62 connect tubular member 20 to the outer wall of stiffening lumen 52.

When median portion 12 is stiffened substantially along its entire length, containing catheter 50 may be inserted into a body conduit. For example, containing catheter 50 may be inserted into a body conduit by placing stiff member distal end 34 in an opening of a body conduit and advancing containing catheter into the body conduit by pushing containing catheter from a portion thereof which is outside the body conduit. If tubular member 20 is sufficiently stiffened, tubular member 20 resists folding or crumpling, thus allowing overcoming friction between containing catheter 50 and the body conduit, and allowing advancing containing catheter into the body conduit.

Figure 3A:
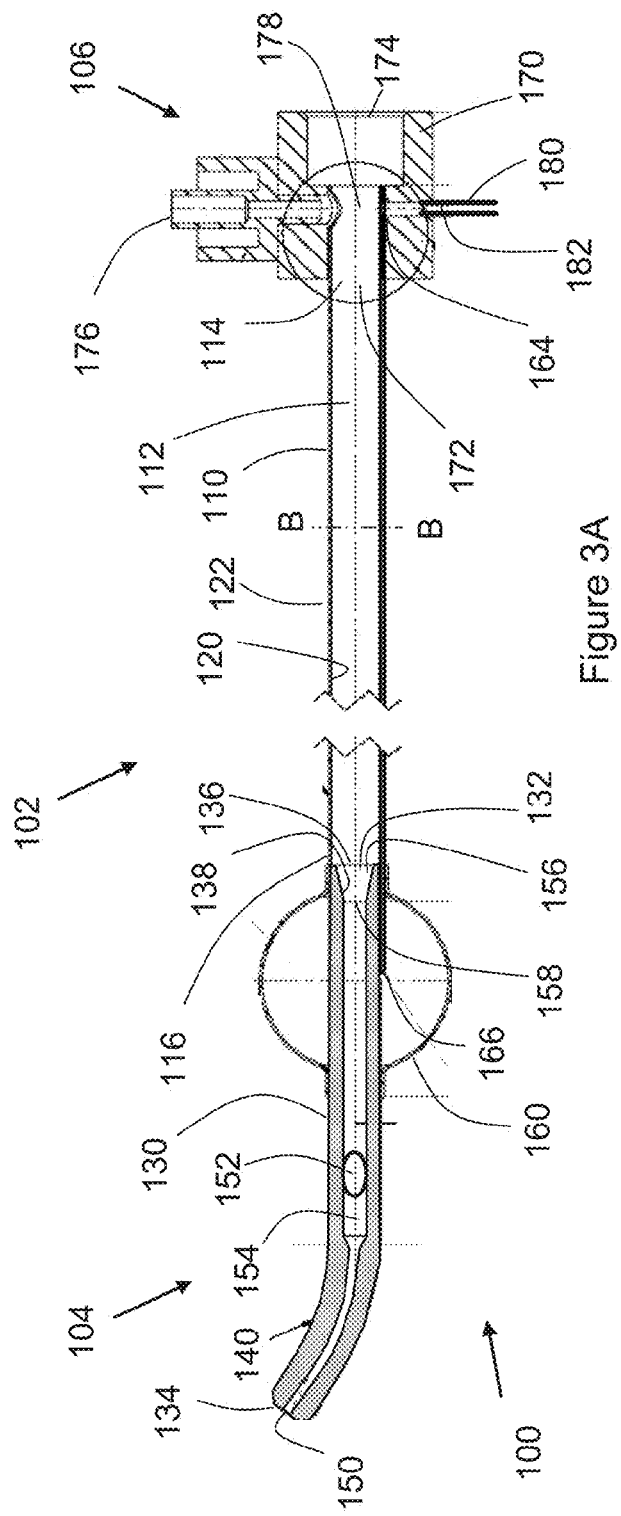
FIG. 3A to 3D schematically depict an embodiment of a containing catheter for facilitating sequential treatment operations in a urethra of a male patient.

FIG. 3A schematically depicts a containing catheter 100 for facilitating sequential treatment operations in a urethra of a male patient, according to an aspect of some embodiments. Containing catheter 100 comprises a median portion 102, a distal portion 104 and a proximal portion 106. Median portion 102 comprises a soft, elongated, tubular member 110. Tubular member 110 comprises a main lumen 112 extending between a proximal end 114 and a distal end 116 of tubular member 110, providing fluid communication between proximal end 114 and distal end 116. Tubular member 110 further comprises an inner surface 120, substantially inside main lumen 112, and an outer surface 122. According to some embodiments tubular member 110 is substantially made of flexible plastics. According to some embodiments, tubular member 110 is substantially made of polyether block amide, for example Pebax® by Arkema. According to some embodiments a thickness of a wall of tubular member 110 (that is the distance between inner surface 120 and outer surface 122) is between about 0.1 mm and about 0.5 mm. According to some embodiments the thickness of the wall of tubular member 110 is about 0.2 mm.

Containing catheter 100 is configured so that distal portion 104 and median portion 102 can be inserted to a urethra of a male's patient. Accordingly, median portion 102 is configured to be stiffened to enable insertion of containing catheter 100 through the urethra, substantially by stiffening tubular member 110, as is further explained and detailed below. Further, during insertion and particularly when median portion is stiffened, the maximal diameter of distal portion 104 and median portion 102 is not more than about 4-6 mm.

Figure 3C:
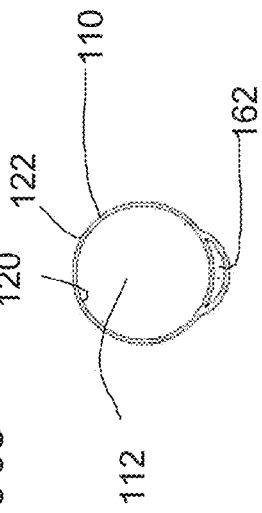
Figure 3B:
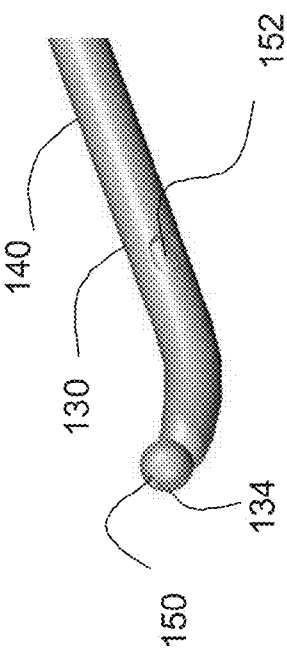

Distal portion 104 comprises a distal stiff member 130, schematically depicted also in a perspective view in FIG. 3B. Distal stiff member 130 extends between a stiff member proximal end 132 and a stiff member distal end 134. Distal stiff member 130 comprises a proximal opening 136 located at stiff member proximal end 132 and comprising a mating surface 138 of a sealed joint.

According to some embodiments distal stiff member 130 is flexible enough to flex during insertion of containing catheter 100 into n urethra, and particularly to conform to the prostatic urethra track up to the bladder. According to some embodiments, distal stiff member 130 is made of flexible plastics. According to some embodiments, distal stiff member 130 is made substantially of latex. According to some embodiments, distal stiff member 130 is made substantially of hard latex. According to some embodiments, distal stiff member 130 is made substantially of silicone.

Distal stiff member 130 is configured as a Tiemann tip, having a substantially curved cylindrical shape having a cylinder side 140 extending between stiff member proximal end 132 and stiff member distal end 134. According to some embodiments distal stiff member 130 is flexible enough to flex during insertion of containing catheter 100 into a male's urethra, to conform to size and track of the urethra along the insertion path and into the bladder. In some embodiments distal stiff member 130 may have a different shape external, configured for specific usages, and adapted to comply with specific constraints associated with insertion into a urethra and as is known in the art. In some embodiments distal stiff member 130 is configured as a Nelaton tip.

Distal stiff member 130 further comprises a first distal opening 150 configured as a guide wire channel and located at stiff member distal end 134, and a second distal opening 152, configured as a drainage hole and located on cylinder side 140. Distal stiff member 130 further comprises a stiff member void 154 inside distal stiff member 130, extending from stiff member proximal end 132 and stiff member distal end 134 substantially along a centre line of distal stiff member 130. Stiff member void 154 thus provides fluid communication between proximal opening 136, first distal opening 150 and second distal opening 152, so as a fluid flowing through any one of the three openings in distal stiff member 130, may flow also through stiff member void 154 and through any of the remaining two openings in distal stiff member 130.

Proximal opening 136 has a conical cross-section, having a wide section 156 at stiff member proximal end 132 and a narrow section 158 facing stiff member void 154. Mating surface 138 is thereby configured as a mating surface for a suitably configured counter conical protrusion (not shown) to form a sealed joint, as is further detailed below.

Containing catheter 100 further comprises an inflatable balloon 160 attached around distal stiff member 130. An inflating lumen 162, also depicted in cross-sectional view FIG. 3C, extends along median portion 102 on outer surface 122 of tubular member 130, between an inflating lumen proximal opening 164 and an inflating lumen distal opening 166. Inflating lumen distal opening 166 is located inside inflatable balloon 160, thus providing fluid communication between the inner volume of inflatable balloon 160 and inflating lumen 162. By pressurizing a fluid such as gas or liquid into inflatable balloon 160 through inflating lumen 162, inflatable balloon may be inflated from a relaxed state to an inflated state. Conversely, inflatable balloon may be deflated from an inflated state to a relaxed state by releasing fluid from within inflatable balloon 160 through inflating lumen 162. In a relaxed state inflatable balloon is substantially empty, thereby causing only a minute increase in the diameter of distal stiff member 130. In an inflated state inflated balloon 160 may contain between about 5 cc to about 30 cc of fluid, and has a diameter larger than the diameter of inflated balloon 160 diameter in a deflated state.

In use, containing catheter 100 may be inserted into a male's urethra so that distal stiff member is advanced through the urethra into the bladder. When inflatable balloon 160 is fully inside the bladder, inflatable balloon 160 may be inflated inside the bladder, thereby preventing undesired retreat of containing catheter 100 in a direction out of the bladder and out of the urethra, thereby inflatable balloon 160 assists in stabilizing containing catheter 100 in place inside the urethra.

Proximal portion 106 of containing catheter 100 comprises a rear connector 170. Rear connector 170 comprises a front opening 172, a rear opening 174 and a side opening 176. A connector void 178 inside rear connector 170 connects and provides fluid communication between front opening 172, rear opening 174 and side opening 176. Rear connector 170 is physically associated with proximal end 114 of tubular member 110, thereby providing fluid communication between main lumen 112 and connector void 178 through front opening 172 of rear connector 170. Further, connector void 178 extends along a substantially straight line between front opening 172 and rear opening 174, thereby enabling insertion of a rigid elongated insertable member through rear opening 174, connector void 178 and 172 front opening into tubular member 110.

Rear connector 170 further comprises an inflating inlet 180. Inflating inlet 180 is in fluid communication with inflating lumen 162 through inflating lumen proximal opening 164. Thus, inflating and deflating inflatable balloon 160 may be carried out by pressurizing a fluid into inflatable balloon 160 through inflating inlet 180 and through inflating lumen 162. Rear connector 170 further comprises an inflating valve 182, e.g. a check valve, in association with inflating inlet 180, for controlling inflating and deflating inflatable balloon 160. Inflating valve 182 may be opened to allow fluid flowing in and out of inflating inlet 180 and thereby allowing inflating and deflating inflatable balloon 160, respectively. Inflating valve 182 may further be close, thereby substantially preventing any fluid flow through inflating inlet 180.

Figure 3D:
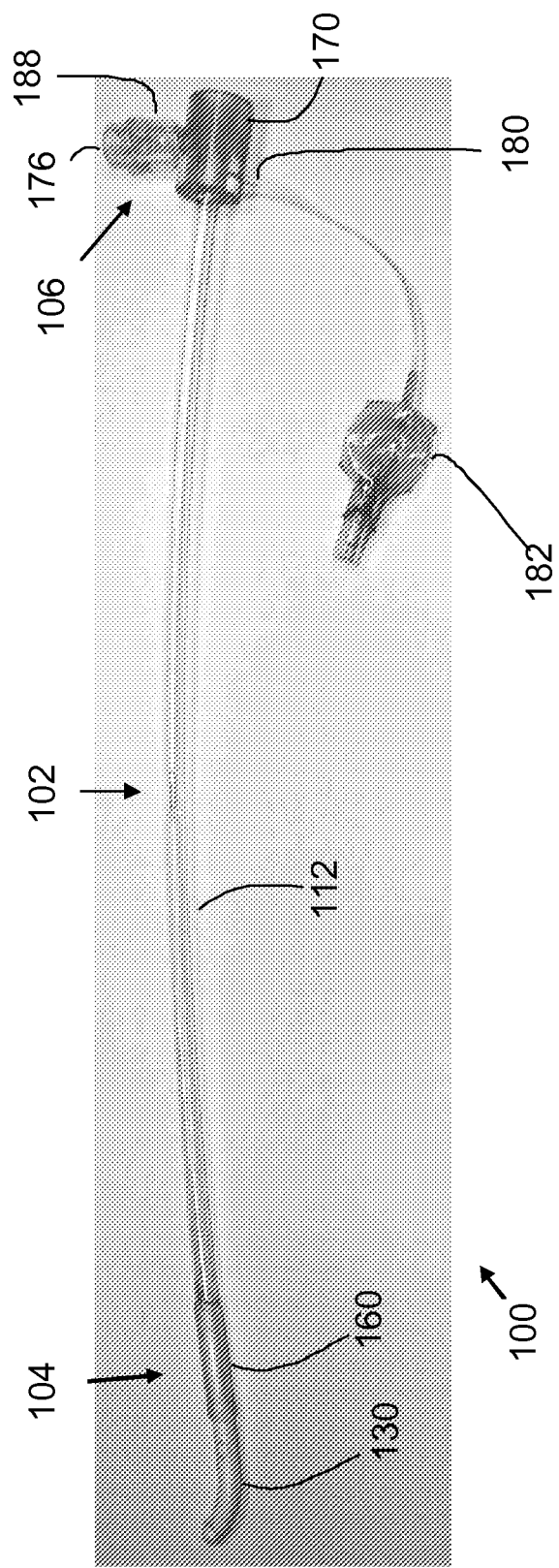

FIG. 3D schematically depicts an embodiment of containing catheter 100 as described herein. Containing catheter 100 comprises median portion 102, comprising tubular member 110 and main lumen 112 therein. Containing catheter 100 further comprises distal portion 104, comprising distal stiff member 130 and inflatable balloon 160, depicted in a relaxed state. Distal stiff member 130 is configured as a Tiemann tip, being curve to facilitate insertion through a prostatic urethra into a patient's bladder. Containing catheter 100 further comprises proximal portion 106, comprising rear connector 170. Rear connector 170 comprises a drain outlet 188 comprising side opening 176, and inflating inlet 180 associated with inflating valve 182, for controlling inflating and deflating inflatable balloon 160 as described above.

FIG. 4A schematically depicts an embodiment of a catheterization apparatus 200, comprising a containing catheter such as containing catheter 100 of FIG. 3, and an elongated introducer inner catheter 210. Introducer inner catheter 210 is insertable into containing catheter 100, having a stiff and flexible portion 212 having a cross-section dimension similar to a cross-section dimension of main lumen 112 of containing catheter 100. Introducer inner catheter 210 extends between an introducer distal end 222 and an introducer proximal end 224, having a length greater than a length of median portion 102 of containing catheter 100. Introducer inner catheter 210 may be inserted into containing catheter 100 by placing introducer distal end 222 at rear opening 174 of rear connector 170 and advancing introducer inner catheter 210 through rear connector void 178 into main lumen 112 of tubular member 110. When introducer inner catheter 210 is inserted into containing catheter 100, introducer proximal end 224 remains outside of containing catheter 100, substantially extending outwards from rear opening 174 of rear connector 170.

Introducer inner catheter 210 is stiff and flexible, thereby being configured to stiffen containing catheter 100 when inserted therein. According to some embodiments introducer inner catheter is made of soft plastics. Catheterization apparatus 200, with introducer inner catheter 210 inserted inside containing catheter 100, is thereby configured for insertion into a male patient's urethra.

Introducer distal end 222 comprises a conical protrusion 226 having an introducer mating surface 228 configured to mate with mating surface 138 of containing catheter 100, to form a sealed joint when introducer inner catheter 210 is inserted into containing catheter 100 and pressed towards distal stiff member 130. Thus, when introducer inner catheter 210 is inserted into containing catheter 100 and pressed towards distal stiff member 130, fluid flowing through stiff member void 154 is prevented from leaking between distal stiff member 130 and introducer inner catheter 210. Further, when conical protrusion 226 is inserted into proximal opening 136 of distal stiff member 130, catheterization apparatus 200 gains mechanical strength by becoming resistant to bending, thereby becoming more suitable for insertion into a patient's urethra.

Introducer inner catheter 210 is hollow, having an inner catheter channel 230, providing fluid communication between an inner catheter distal opening 232 at introducer distal end 222, and an inner catheter proximal opening 234 at introducer proximal end 224. Thus, when introducer inner catheter 210 is inserted inside containing catheter 100 and pressed onto distal stiff member 130, fluid communication is obtained between stiff member void 154 and inner catheter channel 230. Consequently, when catheterization apparatus 200 is inserted into a patient's urethra and advanced so that distal stiff member 130 enters the bladder of the patient, urine from the bladder may flow into stiff member void 154 through drainage hole 152 and flow through inner catheter channel 230 outside through inner catheter proximal opening 234 at introducer proximal end 224, thus signalling a physician using catheterization apparatus 200 that distal stiff member 130 entered the bladder.

FIG. 4B schematically depicts an exemplary use of catheterization apparatus 200 in conjunction with a guide wire 250. Employing a guide wire to assist catheterization might be required in some instances or in some patients, particularly when there are indications for non-regular structure of the urethra, partial blockage or some stricture therein. In such cases a guide wire is first inserted into the urethra and up to the bladder, e.g. using a cystoscope. With the guide wire properly deployed inside the urethra, catheterization apparatus 200, comprising introducer inner catheter 210 inserted inside containing catheter 100, may be guided by guide wire 250. Guide wire 250 is threaded through guide wire channel 150, stiff member void 154, inner catheter channel 230 and inner catheter proximal opening 234. Then catheterization apparatus may be advanced into the urethra guided by guide wire 250, according to well-known insertion practice of known catheters. When catheterization apparatus is stabilized in place, e.g. when distal stiff member 130 is inside the bladder and inflatable balloon 160 is inflated therein, guide wire 250 may be pulled out.

Insertion of catheterization apparatus 200 into the urethra may be carried out using guide wire 250 as described above or using any other method. Further, stabilizing catheterization apparatus 200 in place may be achieved by inflating inflatable balloon 160 inside the bladder or using any other method. After catheterization apparatus 200 is so inserted into the urethra and stabilized in place, introducer inner catheter 210 may be removed from containing catheter 100 by pulling introducer inner catheter 210 outwards, leaving containing catheter 100 deployed inside the urethra.

Figure 5A:
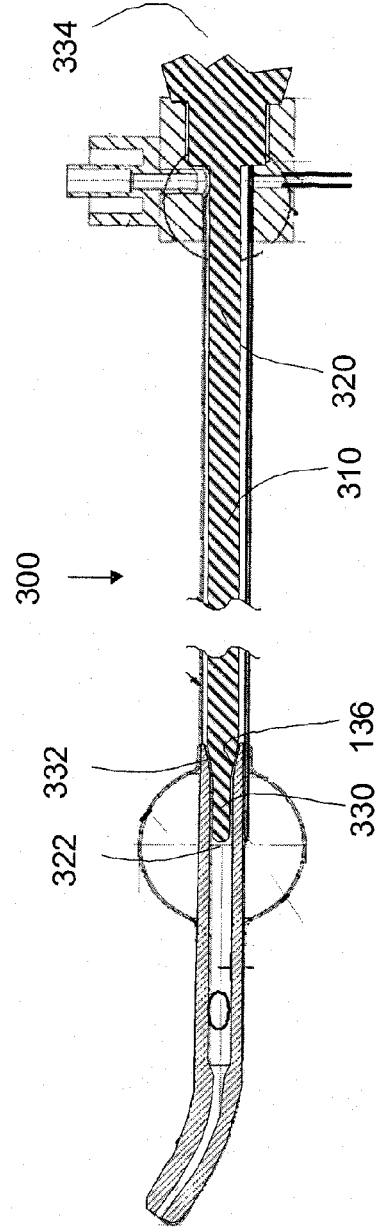
FIG. 5A schematically depicts an embodiment of a catheterization apparatus comprising the containing catheter of FIG. 3, and an embodiment of a rigid inner catheter.
Figure 5B:
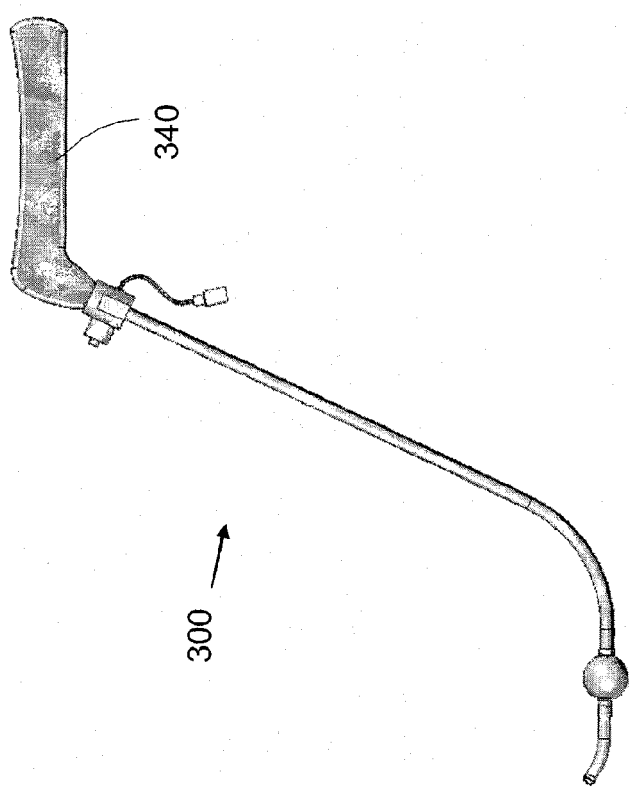
FIG. 5B schematically depicts an embodiment of a rigid inner catheter comprising an external handle.

FIG. 5A schematically depicts an embodiment of a catheterization apparatus 300 comprising a containing catheter such as containing catheter 100 and a rigid inner catheter 310. Rigid inner catheter 310 comprises a rigid pole 320 insertable into containing catheter 100, having a cross-section dimension similar to a cross-section dimension of main lumen 112 of containing catheter 100. Rigid inner catheter 310 extends between a rigid catheter distal end 322 to a length greater than median portion 102 of containing catheter 100. According to some embodiments rigid pole 320 is substantially straight, as schematically depicted in FIG. 5A. According to some embodiments rigid pole 320 is curved to have a desired shape. According to some embodiments rigid pole 320 is curved to have a typical 'hockey stick' shape, as schematically depicted in FIG. 5B.

According to some embodiments, rigid inner catheter 310 may be inserted into containing catheter 100 when containing catheter 100 is deployed inside a male's urethra, e.g. after containing catheter 100 has been inserted into the urethra using an introducer inner catheter such as introducer inner catheter 210 and employing the method described above.

Rigid inner catheter 310 may be inserted into containing catheter 100, by placing rigid catheter distal end 322 at rear opening 174 of rear connector 170 and advancing rigid inner catheter 310 through rear connector void 178 into main lumen 112 of tubular member 110. Rigid inner catheter 310 may thus be advanced into containing catheter 100 until rigid catheter distal end 322 is pressed onto mating surface 138 of distal stiff member 130. When rigid inner catheter 310 is inserted into containing catheter 100, rigid catheter proximal end 324 remains outside of containing catheter 100, substantially extending outwards from rear opening 174 of rear connector 170.

According to some embodiments, catheterization apparatus 300 may be employed to straighten the urethra, or to cause the urethra to conform to a known curve, defined by the shape of rigid pole 320. Straightening the urethra or subjecting the urethra to a pre-defined curve may facilitate various medical procedures. For example insertion of ablation probes in a pre-selected pattern at desired distances from the urethra may be facilitated when the urethra is straight or at least if the urethra location is known. For example, U.S. Pat. No. 7,670,333 and patent application US20090118724 both by Zvuloni et al., disclose apparatus and methods employing a urethral straightener. Such a urethral straightener may comprise a rigid pole having a portion thereof extending outside from the patient's body, and, according to some embodiments, may provide at least two effects. A first effect, resulting from the known spatial relationship between the external portion of the straightener and the portion inside the prostatic urethra, is that the location and orientation of the prostatic urethra is accurately known. A second effect results from forcing the prostatic urethra, into which such a straight section has been placed, into a straight linear orientation, thereby creating a desirable arrangement wherein that prostatic urethra is both straightened and in a known position. Such a technique may thus greatly facilitate procedures of treatments of the urethra. For example localizing a focused treatment such as ablation by ablation needles or inserting probes at a desired distance from the urethra, may be facilitated by inserting the needles or the probes parallel to the known direction of the straightened urethra and at a predetermined distance therefrom.

Rigid pole 320 of rigid inner catheter 310 is made of a rigid material. Moreover, various embodiments of rigid inner catheter 310 may be employed in conjunction with various types of instrumentation and technologies, in connection with various treatment procedures. For example, rigid inner catheter 310 may be employed in conjunction with an ultrasound imaging modality employed to image the prostate; or in conjunction with an X-ray imaging modality; or in conjunction with yet another type of imaging modality. Accordingly, embodiments of rigid pole 320 may be made echogenic to an imaging technique being employed, thereby facilitating imaging of rigid pole 320, and hence imaging of the prostatic urethra, with the imaging modality used. Generally, imaging a body conduit at or near a treatment site may significantly reduce risk of damage to the body conduit. Specifically, imaging the prostatic urethra during treatment often reduces risk of urethral injury during e.g. trans-perineal probe insertion or needle insertion or during trans-rectal needle insertion (for example for trans-rectal prostate biopsy).

Rigid catheter distal end 322 comprises a conical protrusion 330 having a rigid catheter mating surface 332. Conical protrusion 330 fits into conical proximal opening 136 at stiff member proximal end 132. Thus, rigid catheter mating surface 332 and mating surface 138 of stiff member proximal end 132 form together a sealed joint when rigid inner catheter 310 is pressed onto distal stiff member 130. Further, rigid catheter distal end 322 is blind, having e.g. no holes through, thereby preventing any flow through proximal opening 136, when rigid inner catheter 310 is pressed onto distal stiff member 130.

FIG. 5B schematically depicts an embodiment of catheterization apparatus 300, wherein rigid inner catheter 310 further comprises an external handle 340. External handle 340 is fixedly attached at rigid catheter proximal end 324, allowing a user to manipulate rigid inner catheter 310 inside the urethra. External handle 340 may further be used to mechanically attach external instrumentation to rigid inner catheter 310 as is further explained below.

Figure 5C:
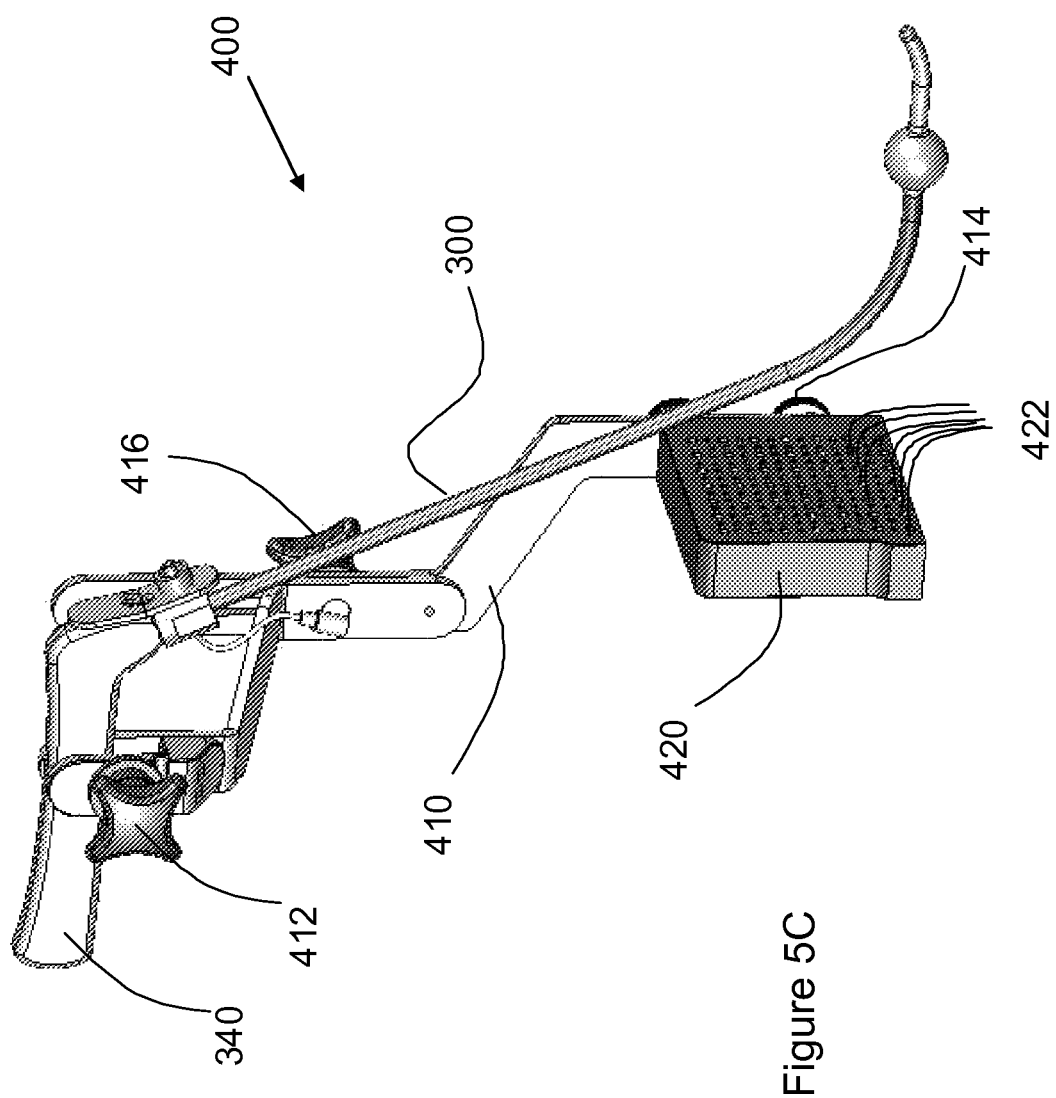
FIG. 5C schematically depicts an embodiment of a catheterization apparatus comprising the rigid inner catheter of FIG. 5B, and a positioning template mechanically attached thereto.

FIG. 5C schematically depicts an embodiment of catheterization apparatus 400, configured for facilitating aiming a treatment tool to a treatment locus having a known spatial relationship with the urethra. Catheterization apparatus 400 comprises substantially catheterization apparatus 300 of FIG. 5B, and further comprises a mechanical arm 410 mechanically attached to external handle 340 using a first knob 412. The mechanical attachment of mechanical arm 410 to external handle 340 may be controllably modified by a user. A user may establish a desired positioning of mechanical arm 410 relative to external handle 340, e.g. by attaching mechanical arm 410 at a desired point on external handle 340 and locking first knob 412. Further, a user may establish a desired orientation of mechanical arm 410 relative to external handle 340, e.g. by selecting such a desired orientation and locking first knob 412 so as to fix that desired orientation.

Catheterization apparatus 400 further comprises a positioning template 420, mechanically attached to mechanical arm 410 by a second knob 414. Positioning template 420 comprises an array of apertures 422 appropriately sized for accommodating a dense array of biopsy needles (not shown) serving as a plurality of treatment tools. A user may establish a desired position of positioning template 420 relative to mechanical arm 410, e.g. by attaching positioning template 420 at a desired point on mechanical arm 410 and locking second knob 414. Further, a user may establish a desired orientation of positioning template 420 relative to mechanical arm 410, e.g. by selecting such a desired orientation and locking second knob 414 so as to fix that desired orientation. A third knob 416 may be used to modify a total length of mechanical arm 410 and fix mechanical arm 410 at a desired total length. Thus, position and orientation of positioning template 420 relative to rigid pole 320 can be established by a user by controllably modifying at least one of the mechanical attachments described above. For example, a user may aim a treatment tool attached to positioning template 420 to a treatment locus having a known spatial relationship with rigid pole 320.

Various embodiments of catheterization apparatus 400 may comprise positioning templates different from positioning template 420 of FIG. 5C. Depending on a treatment tool and a treatment procedure to be employed, a suitable embodiment of position template 420, configured to be attached to the selected treatment tool, may be selected to be attached to mechanical arm 410.

For use, catheterization apparatus 400 may be employed to aim a selected treatment tool to a desired treatment locus in a patient's body by carrying out the following steps:

Providing a containing catheter such as containing catheter 100, and inserting the containing catheter into a patient's urethra, e.g. by using an introducer inner catheter such as introducer inner catheter 210, and then removing the introducer inner catheter from the containing catheter.

Providing a rigid inner catheter such as rigid inner catheter 310, and mechanically attaching a mechanical arm such as mechanical arm 410 to a rigid catheter proximal end thereof.

Selecting a treatment tool, suitable for a treatment procedure to be used, and selecting a positioning template configured to be fixedly attached to the treatment tool.

Mechanically attaching the positioning template with the treatment tool fixedly attached thereto to the mechanical arm.

Using the modifiable mechanical attachment of the mechanical arm to the rigid inner catheter and the modifiable mechanical attachment of the positioning template to the mechanical arm, aiming the treatment tool to a locus having a pre-determined spatial relationship with the rigid pole of the rigid inner catheter.

Inserting the rigid inner catheter into the containing catheter, deployed inside the patient's urethra.

Using the treatment tool to apply a treatment to a locus in the patient's body having the pre-determined spatial relationship with the location of the rigid pole inside the patient's urethra.

According to aspects of some embodiments of a catheterization apparatus such as catheterization apparatus 300, aiming a treatment tool to a locus having a pre-determined spatial relationship with rigid pole 320 inside the urethra may be carried out without a mechanical connection between rigid inner catheter 310 and positioning template 420. According to some embodiments, rigid inner catheter 310 comprises a transmitter of electromagnetic waves located near rigid catheter distal end 322. A power source configured to provide power for activating the transmitter is located near rigid catheter proximal end 324 and electrically associated with the transmitter by wires deployed along rigid pole 320. An electromagnetic receiver, configured for receiving electromagnetic signals from the transmitter, is arranged on positioning template 420. By analyzing signals received by the receiver, positioning template may be aligned to have a desired position and orientation relative to the transmitter in rigid pole 320, thereby allowing aiming a treatment tool fixedly attached to positioning template 420 to a desired locus having a pre-defined spatial relationship with rigid pole 320. Additional embodiments allowing aiming a treatment tool to a treatment locus using a rigid inner catheter are disclosed in patent U.S. Pat. No. 7,670,333 and patent application US20090118724 both by Zvuloni et al.

Figure 6:
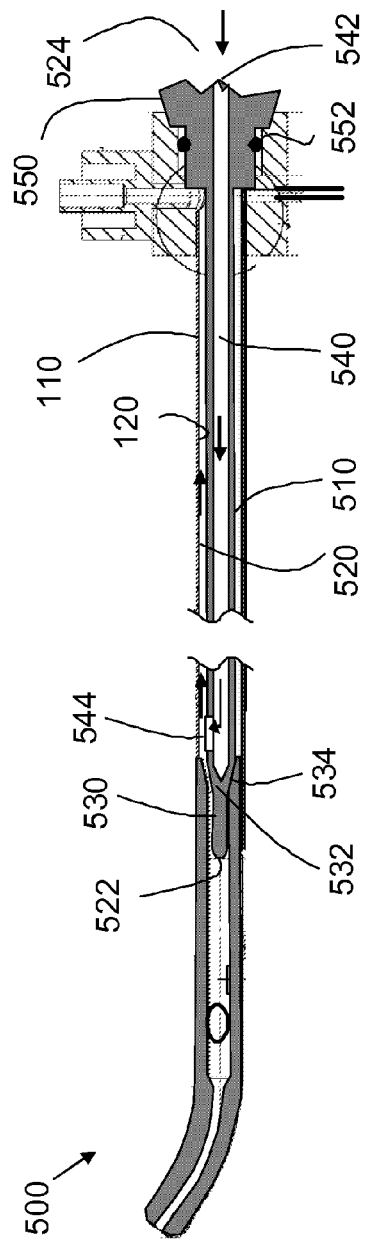
FIG. 6 schematically depicts an embodiment of a catheterization apparatus comprising the containing catheter of FIG. 3 and a flow inner catheter.

FIG. 6 schematically depicts an embodiment of a catheterization apparatus 500 comprising a containing catheter such as containing catheter 100 and a flow inner catheter 510. Flow inner catheter 510 is insertable into containing catheter 100, having a cross-section dimension smaller than a cross-section dimension of main lumen 112 of containing catheter 100. Thus, when flow inner catheter 510 is inserted into main lumen 112 of containing catheter 100, a gap 520 is formed between flow inner catheter 510 and inner surface 120 of tubular member 110, allowing fluid flow therethrough. Flow inner catheter 510 extends between a flow catheter distal end 522 to a length greater than a length of median portion 102 of containing catheter 100.

According to some embodiments, flow inner catheter 510 may be inserted into containing catheter 100 when containing catheter 100 is deployed inside a male's urethra, e.g. after containing catheter 100 has been inserted into the urethra using an introducer inner catheter such as introducer inner catheter 210 and employing the methods described above.

Flow inner catheter 510 may be inserted into containing catheter 100, by placing flow catheter distal end 522 at rear opening 174 of rear connector 170 and advancing flow inner catheter 510 through rear connector void 178 into main lumen 112 of tubular member 110. Flow inner catheter 510 may thus be advanced into containing catheter 100 until flow catheter distal end 522 is pressed onto mating surface 138 of distal stiff member 130. When flow inner catheter 510 is inserted into containing catheter 100, flow catheter proximal end 524 remains outside of containing catheter 100, substantially extending outwards from rear opening 174 of rear connector 170.

According to some embodiments catheterization apparatus 500 may be employed for controllably streaming a fluid through the urethra as is explained in detail further below. According to some embodiments, such a fluid flowing through flow inner catheter 510 and through the urethra may be thermally controlled. According to some embodiments, streaming a thermally controlled fluid through the urethra may be employed for protecting the urethra during a medical procedure. According to some embodiments, a warming fluid may be forced through flow inner catheter 510 to protect the urethra during cryosurgical ablation of prostate tissue near the prostatic urethra. According to some embodiments, a cooling fluid may be forced through flow inner catheter 510 to protect the urethra during RF ablation, microwave ablation or High Intensity Focused Ultrasound (HIFU) ablation of prostate tissue near the prostatic urethra.

Flow catheter distal end 522 comprises a protruding tip 530 comprising a conical section 532 having a flow catheter mating surface 534 of a sealed joint. Protruding tip 530 is configured to insert into stiff member void 154 through proximal opening 136 when flow inner catheter is inserted into containing catheter 100 and pressed onto distal stiff member 130. Conical section 532 fits into conical proximal opening 136 at stiff member proximal end 132. Thus, flow catheter mating surface 534 and mating surface 138 at stiff member proximal end 132 form together a sealed joint when flow inner catheter 510 is pressed onto distal stiff member 130. Further, protruding tip 530 is blind, having e.g. no holes through, thereby preventing any flow through proximal opening 136, when flow inner catheter 510 is pressed onto distal stiff member 130.

Flow inner catheter 510 is hollow, having an inner catheter channel 540, providing flow communication between a flow catheter proximal opening 542 and a flow catheter distal opening 544. Flow catheter distal opening 544 is arranged proximal to flow catheter distal end 522 and facing gap 520 between flow inner catheter 510 and inner surface 120 of tubular member 110. Thus, when flow inner catheter 510 is inserted into containing catheter 100 and pressed onto distal stiff member 130, fluid communication is provided between inner catheter channel 540 and gap 520 through flow catheter distal opening 544.

Flow inner catheter 510 further comprises an external member 550 at flow catheter proximal end 524. External member 550 is configured to fit into rear opening 174 of rear connector 170. When flow inner catheter 510 is inserted into containing catheter 100 and fully advanced therein until flow catheter distal end 522 is pressed onto distal stiff member 130, external member 550 fits into rear opening 174 of rear connector 170 and an O-ring 552 seals and prevents fluid leaks between external member 550 and rear opening 174.

Figure 7:
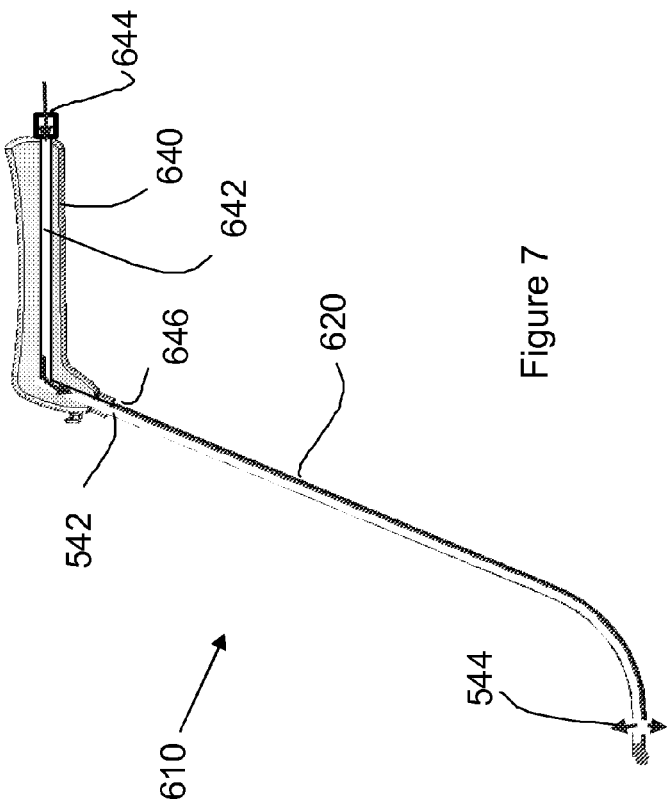
FIG. 7 schematically depicts an embodiment of a flow inner catheter comprising a rigid portion, and FIGS. 8A and 8B schematically depict an embodiment of a catheterization apparatus comprising a containing catheter and a flow inner catheter and having two operational states according to an arrangement of the flow inner catheter inside the containing catheter.

FIG. 7 schematically depicts a flow inner catheter 610 according to an aspect of some embodiments. Flow inner catheter 610 has functionality similar to that of flow inner catheter 510. Additionally, flow inner catheter 610 comprises a hollow rigid pole 620, thereby being configured to be rigid, having a pre-determined shape similar to that of rigid inner catheter 310. Thus, according to some embodiments, flow inner catheter 610 is configured to straighten the urethra, or to cause the urethra to conform to a known curve, defined by the shape of hollow rigid pole 620, when flow inner catheter is inserted in a containing catheter (not shown) deployed inside a patient's urethra.

Flow inner catheter 610 comprises an external handle 640. External handle 640 is fixedly attached at flow catheter proximal end 524, allowing a user to manipulate flow inner catheter 610 inside the urethra. External handle 640 may further be used to mechanically attach external instrumentation to flow inner catheter 610, as explained above regarding rigid inner catheter 310 and catheterization apparatus 400 in FIGS. 5A-5C. External handle 640 is hollow, comprising a handle channel 642 providing fluid communication between a handle proximal opening 644 and a handle distal opening 646. External handle 640 is attached at flow catheter proximal end 524 so that handle distal opening 646 is coupled with flow catheter proximal opening 542 thereby providing fluid communication between handle proximal opening 644 and flow catheter distal opening 544 through hollow rigid pole 620 and through inner catheter channel 540 therein. A fluid connector 648 is attached to external handle 640 coupled with handle proximal opening 644, to allow quick connection to flow inner catheter 610 of further instrumentation having a suitable fluid connector.

Thus, according to some embodiments, a catheterization apparatus comprising a containing catheter such as containing catheter 100 and flow inner catheter 610 may be employed for facilitating treatment at a treatment site, e.g. in the prostate near the urethra. According to some embodiments, the containing catheter is inserted and deployed inside the patient's urethra, e.g. as is explained above. Flow inner catheter 610 is inserted into the containing catheter, thereby straightening the urethra or otherwise conforming the urethra to a pre-determined known curve. According to some embodiments hollow rigid pole 620 is configured to be echogenic to an imaging technique being employed, for example for ultrasound imaging. Thus, for example under ultrasound imaging, visualizing hollow rigid pole 620 reveals the prostatic urethral tract, and cryosurgical ablation or HIFU or RF ablation may be applied to prostate tissue while avoiding regions proximal the urethra. Furthermore, a thermally controlled fluid may be forced through flow inner catheter 620 to stabilize the temperature of the urethra and the urethra's immediate vicinity, including e.g. nerves, during the ablation process, and thereby protect the urethra and its immediate vicinity from thermal damage as is explained above regarding flow inner catheter 510. For example, fluid may be forced through handle proximal opening 644, through hollow rigid pole 620, through flow catheter distal opening 544 and circulated back through gap 520 (not shown) between hollow rigid pole 620 and inner surface 120 of tubular member 110 of the containing catheter (not shown) as is explained above regarding flow inner catheter 510.

FIGS. 8A and 8B schematically depict an embodiment of a catheterization apparatus 700, comprising a flow inner catheter 710 and a containing catheter 750. Catheterization apparatus 700 is operable in a first operational state and in a second operational state, according to the arrangement of flow inner catheter 710 inside containing catheter 750. In the first operational state thereof, catheterization apparatus 700 may serve to support a treatment procedure involving e.g. forcing fluid flowing through flow inner catheter, substantially as described above regarding e.g. catheterization apparatus 500 and flow inner catheter 610. In the second operational state thereof catheterization apparatus 700 may serve to support e.g. a post-treatment drainage procedure as is further detailed and explained below.

Flow inner catheter 710 is different from flow inner catheter 510 by having a drainage proximal opening 712 at flow catheter proximal end 524, in addition to flow catheter proximal opening 542. Flow inner catheter 710 further comprises a three-way valve 714, having a first operational state and a second operational state. Three-way valve 714 is configured and operable to selectively provide fluid communication between inner catheter channel 540 and flow catheter proximal opening 542 in the first operational state thereof, and to selectively provide fluid communication between inner catheter channel 540 and drainage proximal opening 712 in the second operational state thereof.

Containing catheter 750 is different from containing catheter 100 in having a two-state rear connector 752 instead of rear connector 170. Two state rear connector 752 is configured to support two distinct arrangements of flow inner catheter 710 inside containing catheter 750, thereby allowing catheterization apparatus 700 to operate in the first operational state and in the second operational state described above. Connector void 178 in two-state rear connector 752 comprises a connector chamber 754 configured to encompass external member 550 of flow inner catheter 710. External member 550 is operable to slide inside connector chamber 754 by pushing and pulling flow inner catheter 710 relative to containing catheter 750 from a first arrangement thereof to a second arrangement thereof and vice versa. O-ring 552 seals and prevents fluid leaks between external member 550 and rear opening 174 while flow inner catheter 710 is in the first arrangement or in the second arrangement thereof.

Catheterization apparatus 700 is operable in the two operational states mentioned above when, e.g., catheterization apparatus 700 is suitably deployed inside a patient's urethra and distal stiff member 130 is inside the bladder, as described above. In the first arrangement, depicted schematically in FIG. 8A and corresponding to the first operational state of catheterization apparatus 700, flow inner catheter 710 is pushed and advanced into containing catheter 750 until protruding tip 530 at flow catheter distal end 522 inserts into conical proximal opening 136 at stiff member proximal end 132. Flow catheter mating surface 534 and mating surface 138 at stiff member proximal end 132 form together a sealed joint thereby preventing any flow through proximal opening 136. Particularly, urine flow from the bladder through conical proximal opening 136 is prevented.

In the first operational state, three-way valve 714 selectively provides fluid communication between inner catheter channel 540 and flow catheter proximal opening 542. Thus, fluid may be forced for example into flow catheter proximal opening 542. The fluid then flows through inner catheter channel 540 towards flow catheter distal end 530, exits inner catheter channel 540 through flow catheter distal opening 544, flows in gap 520 inside main lumen 112 towards two-state rear connector 752 and exits through side opening 176 of two state rear connector 752. In some embodiments fluid may be forced to flow substantially along the same track in the opposite direction. According to some embodiments, catheterization apparatus 700 may thus serve in the first operation state to support a treatment procedure by stabilizing the temperature of the urethra during an ablation procedure applied to prostatic tissue proximal to the urethra, as is described above regarding FIGS. 6 and 7.

In the second operational state, depicted schematically in FIG. 8B, three-way valve 714 selectively provides fluid communication between inner catheter channel 540 and drainage proximal opening 712. Accordingly, fluid flow through catheter proximal opening 542 is prevented. Further, flow inner catheter 710 is pulled backwards and retreated inside containing catheter 750 so that protruding tip 530 at flow catheter distal end 522 disengages from conical proximal opening 136 and flow catheter mating surface 534 disengages from mating surface 138. Thus, fluid communication between stiff member void 154 and main lumen 112 of containing catheter 750 through proximal opening 136 is enabled. Flow may further continue through flow catheter distal opening 544 into inner catheter channel 540 and out through drainage proximal opening 712. In the second operational state thereof catheterization apparatus 700 may thus serve to support e.g. a post-treatment drainage procedure as urine from the bladder is enabled to flow out through catheterization apparatus 700 to be collected e.g. at drainage proximal opening 712. It is emphasized that—compared to currently known treatment procedures involving inserting a first catheter for supporting e.g. an ablation procedure, then removing the first catheter and inserting a second catheter to support a drainage procedure during a post-treatment recovery period—catheterization apparatus 700 provides at least two distinct advantages. First by employing a containing catheter such as containing catheter 750 (or, for that matter, such as containing catheter 100), inserting and removing of various inner catheters generates minimal risk or even no risk at all to the urethra. Second, catheterization apparatus 700 may support two sequential procedures without removing any catheter from the patient's body, not even removing an inner catheter from within a containing catheter. Employing catheterization apparatus 700 for this end thus requires only a relatively minute change of arrangement of flow inner catheter 710 inside containing catheter 750, substantially by displacing one relative to the other, thereby further facilitating the medical procedure and reducing procedure time.

Thus, according to an aspect of some embodiments there is provided a containing catheter (10, FIG. 1A, 100 FIG. 3A) for facilitating sequential treatment operations, comprising a median portion (12, 102) comprising an elongated, substantially tubular member (20, 110), having a main lumen (22, 112) therein. The main lumen extends between a proximal end (24, 114) and a distal end (26, 116) of the tubular member, thereby providing fluid communication between the proximal end and the distal end of the tubular member;

The containing catheter further comprises a distal portion (14, 104), comprising a distal stiff member (30, 130) extending between a stiff member proximal end (32, 132) and a stiff member distal end (34, 134). The distal stiff member comprises a proximal opening (36, 136) located at the stiff member's proximal end whereas the proximal opening further comprises a mating surface (38,138) of a sealed joint. The distal stiff member further comprises a distal opening (40, 150), and a stiff member void (42, 152) inside the stiff member, configured to provide fluid communication between the proximal opening and the distal opening. The distal portion is physically associated with the median portion so that the stiff member void of the distal stiff member is in fluid communication with the main lumen.

According to some embodiments, the tubular member (20, 110) is stiff and flexible. According to some embodiments, the tubular member (20, 110) is soft, and the median portion is configured to be stiffened to enable insertion of the containing catheter through a body conduit. According to some embodiments, the containing catheter further comprises at least one stiffening lumen 52 extending at least along the tubular member 20 of the median portion 12 between a stiffening lumen proximal end 56 and a stiffening lumen distal end 54. The stiffening lumen comprises a single stiffening lumen opening 58 at the stiffening lumen proximal end 56 allowing to pressurize a fluid into the stiffening lumen and thereby to stiffen the tubular member and hence to stiffen the median portion.

According to some embodiments, the distal stiff member (30, 130) is flexible. According to some embodiments, the distal stiff member comprises latex. According to some embodiments, the distal stiff member comprises hard latex. According to some embodiments, the distal stiff member comprises silicone.

According to some embodiments, the containing catheter (10, 100) is coated on at least a portion of an inner surface (44, 120) of the tubular member (20, 11) by a biocompatible lubricant, thereby reducing friction between the inner surface and an insertable member inserted therein. According to some embodiments, the biocompatible lubricant comprises hydrophilic material layer. According to some embodiments, the containing catheter (10, 100) is coated on at least a portion of an outer surface (46, 122, 140) thereof by a biocompatible hydrophilic material layer, thereby reducing friction during insertion of the containing catheter into a body conduit.

According to some embodiments, the containing catheter 100 further comprises a proximal portion 106 comprising a rear connector 170 having a front opening 172, a rear opening 174, a side opening 176 and a connector void 178 inside. The connector void provides fluid communication between the front opening, the rear opening and the side opening. The rear connector is physically associated with the proximal end 114 of the tubular member 110, thereby providing fluid communication between the main lumen 112 and the connector void 178.

According to some embodiments, the containing catheter 100 further comprises at least one stiffening lumen extending at least along the tubular member 110 of the median portion 102 between a stiffening lumen proximal end and a stiffening lumen distal end, having a single stiffening lumen opening at the stiffening lumen proximal end allowing to pressurize a fluid into the stiffening lumen and thereby to stiffen the tubular member 110 and hence to stiffen the median portion 102. According to some embodiments, the rear connector 170 comprises a pressure inlet having a fluid communication with the stiffening lumen through the stiffening lumen opening, allowing pressurizing a fluid into the stiffening lumen through the pressure inlet.

According to some embodiments, the connector void 178 extends along a substantially straight line between the front opening 172 and the rear opening 174 thereby enabling insertion of a rigid elongated pole through the rear opening, the connector void and the front opening into the tubular member.

According to some embodiments, the proximal opening 136 has a conical cross-section having a wide section 156 at the stiff member proximal end 132 and a narrow section 158 coupled to the stiff member void 154. Proximal opening 136 has a smooth mating surface 138 in between the wide section and the narrow section, thereby being configured as a mating surface for a suitably configured counter conical protrusion to form a sealed joint.

According to some embodiments, the distal stiff member 130 is configured substantially as a cylinder having a cylinder side 140 extending between the stiff member proximal end 132 and the stiff member distal end 134. According to some embodiments, the stiff member void 154 extends from the proximal opening 136 to the distal opening 150 substantially along a centre line of the distal stiff member. According to some embodiments, the cylinder 130 is curved. According to some embodiments, the distal opening 150 is located on the cylinder side 140. According to some embodiments, the distal opening 150 is located on the stiff member distal end 134. According to some embodiments, the distal opening 150 is configured as a guide wire channel thereby allowing inserting the containing catheter 100 into a body conduit guided along a guide wire (250, FIG. 4B) passing through the stiff member void 154. According to some embodiments, the containing catheter comprises a distal stiff member opening 152 on the cylinder side 140 of the distal stiff member 130, and wherein the stiff member void 154 provides fluid communication between the proximal opening, the distal opening and the distal stiff member opening.

According to some embodiments the containing catheter further comprises an inflatable balloon attached around an outer surface of the distal portion. The containing catheter further comprises an inflating lumen extending at least along the median portion between an inflating lumen proximal opening and an inflating lumen distal opening. The inflating lumen distal opening is located inside the inflatable balloon. The inflatable balloon can be inflated and deflated through the inflating lumen between a relaxed state, having a first outer radius and an inflated state having a second outer radius larger than the first outer radius.

According to some embodiments the containing catheter further comprises a proximal portion comprising a rear connector having an inflating inlet in fluid communication with the inflating lumen, thereby enabling inflating and deflating the inflatable balloon through the inflating inlet.

According to some embodiments the containing catheter is configured for facilitating sequential treatment operations in a urethra of a male patient. The distal stiff member is flexible, and the tubular member has a diameter between about 3 mm and 6 mm, thereby rendering the containing catheter insertable through the urethra to a patient's bladder. The inflatable balloon is configured as a Foley balloon, inflatable to a volume between about 5 cc to about 30 cc for stabilizing the containing catheter in the urethra by being inflated in the bladder. According to some embodiments the distal portion comprises a Tiemann tip. According to some embodiments the distal portion comprises a Nelaton tip.

According to an aspect of some embodiments there is provided a catheterization apparatus comprising the containing catheter as described above and an elongated inner catheter insertable into the main lumen of the containing catheter. The elongated inner catheter extends between an inner catheter proximal end and an inner catheter distal end, having a length greater than a length of the median portion of the containing catheter.

According to some embodiments the inner catheter has a cross-section dimension similar to a cross-section dimension of the main lumen.

According to some embodiments the inner catheter comprises a stiff and flexible portion, enabling to stiffen the tubular member when inserted therein and allowing inserting such stiffened containing catheter into a body conduit.

According to some embodiments the inner catheter distal end comprises an inner catheter mating surface configured to fit the mating surface of the proximal opening at the stiff member proximal end to form a sealing joint when the inner catheter is inserted into the containing catheter and pressed onto the stiff member.

According to some embodiments the inner catheter distal end is blind thereby preventing fluid flow through the proximal opening of the distal stiff member when the inner catheter is inserted into the containing catheter and pressed onto the distal stiff member.

According to some embodiments the inner catheter is hollow, having an inner catheter channel between a proximal catheter opening and a distal catheter opening.

According to some embodiments the distal catheter opening is at the inner catheter distal end, configured to fit the mating surface of the proximal opening at the distal stiff member to form a sealing joint, allowing fluid communication between the inner catheter channel and the stiff member void, when the inner catheter is inserted into the containing catheter and pressed onto the stiff member.

According to some embodiments the inner catheter has a cross-section dimension smaller than a cross-section dimension of the main lumen, thereby forming a gap between the inner catheter and an inner surface of the tubular member, when the inner catheter is inserted into the tubular member.

According to some embodiments the inner catheter distal end is blind, thereby preventing fluid flow through the proximal opening of the distal stiff member. The distal catheter opening is proximal to the inner catheter distal end and facing the gap between the inner catheter and the inner surface of the tubular member. Thereby fluid communication between the inner catheter channel and the gap through the inner catheter distal opening is provided when the inner catheter is inserted into the containing catheter and pressed onto the distal stiff member.

According to some embodiments the catheterization apparatus is operable in at least two operational states according an arrangement of the inner catheter inside the containing catheter. In a first operational state the inner catheter is inserted into the containing catheter and advanced until the inner catheter distal end is pressed onto the mating surface of the proximal opening of the distal stiff member.

A fluid forced into the inner catheter hollow channel flows towards the inner catheter distal end inside the inner catheter hollow channel, exits the inner catheter hollow channel through the distal catheter opening, and flows in the gap inside the main lumen towards the proximal end. Fluid flow through the proximal opening of the distal stiff member is prevented. In a second operation stated the inner catheter is retreated inside the containing catheter so that the inner catheter distal end disengages from the mating surface of the proximal opening of the distal stiff member. Fluid communication is thus provided between the stiff member void and the main lumen of the containing catheter through the proximal opening.

According to some embodiments the inner catheter comprises a rigid pole insertable into the containing catheter, and extends between the inner catheter distal end to a length greater than the median portion of the containing catheter.

According to some embodiments the catheterization apparatus further comprises an external handle fixedly attached to the inner catheter allowing a user to manipulate the inner catheter during insertion into the containing catheter inside a body conduit.

According to some embodiments the catheterization apparatus further comprises a mechanical arm mechanically attached to the inner catheter proximal to the inner catheter proximal end. The catheterization apparatus further comprises a positioning template mechanically attached to the mechanical arm and configured to fixedly attach to a treatment tool. Position and orientation of the positioning template relative to the rigid pole can be established by a user by controllably modifying at least one of the mechanical attachments, thereby allowing aiming a treatment tool attached to the positioning template to a treatment locus having a known spatial relationship with the rigid pole.

According to an aspect of some embodiments there is provided a method of catheterization. The method comprises providing a containing catheter as described above, stiffening the median portion of the containing catheter, and inserting the stiffened containing catheter into a body conduit of a patient.

According to some embodiments the method further comprises prior to the inserting step providing a first inner catheter insertable into the main lumen of the containing catheter, and having a stiff and flexible portion. The method further comprises stiffening the containing catheter by inserting the first inner catheter into the main lumen of the containing catheter and pressing the first inner catheter onto the distal stiff member. The method further comprises following the inserting step removing the first inner catheter from the containing catheter while the containing catheter is inside the body conduit.

According to some embodiments the method further comprises providing a second inner catheter having a cross-section dimension smaller than a cross section dimension of the main lumen of the containing catheter. The second inner catheter is further hollow, having an inner catheter channel between a proximal catheter opening and a distal catheter opening. An inner catheter distal end is blind, adapted to fit the mating surface of the proximal opening at the stiff member proximal end to form a sealing joint. The method further comprises inserting the second inner catheter into the containing catheter and pressing the second inner catheter onto the distal stiff member, thereby preventing fluid flow through the proximal opening of the distal stiff member. The method further comprises forcing a fluid into one of the inner catheter channel and the main lumen, and collecting the forced fluid from the other of the inner catheter channel and the main lumen.

According to some embodiments the method further comprises retreating the second inner catheter inside the containing catheter so that the inner catheter distal end disengages from the mating surface of the proximal opening of the distal stiff member, thereby allowing fluid communication between the stiff member void and the main lumen of the containing catheter through the proximal opening.

According to some embodiments the method further comprises providing a second inner catheter comprising a rigid pole insertable into the containing catheter. the rigid pole extends between an inner catheter distal end to a length greater than the median portion of the containing catheter. The method further comprises inserting the second inner catheter into the containing catheter and pressing the second inner catheter onto the distal stiff member, thereby establishing a known spatial relationship between a proximal portion of the rigid pole and the portion of the body conduit containing the containing catheter. The method further comprises providing a mechanical arm and mechanically attaching the mechanical arm to the rigid pole at the proximal portion thereof. The method further comprises providing a positioning template configured to fixedly attach to a treatment tool and mechanically attaching the positioning template to the mechanical arm. The method further comprises fixedly attaching a treatment tool to the positioning template, and aiming the treatment tool to a treatment locus having a known spatial relationship with the portion of the body conduit containing the containing catheter, by controllably modifying at least one of the mechanical attachments.

According to an aspect of some embodiments there is provided a catheterization apparatus for facilitating sequential treatment operations therethrough. The catheterization apparatus comprises a containing catheter comprising an elongated, substantially tubular member of a soft material. The tubular member comprises a main lumen therein extending between a proximal end and a distal end of the tubular member thereby providing fluid communication between the proximal end and the distal end of the tubular member. The containing catheter further comprises a distal stiff member coupled to the tubular member at the distal end. The distal stiff member comprises a proximal opening facing the tubular member thereby having fluid communication with the main lumen. The catheterization apparatus further comprises an elongated inner catheter insertable into the containing catheter. The elongated inner catheter comprises a stiff and flexible portion, having a cross-section dimension similar to a cross section dimension of the main lumen. The elongated inner catheter further comprises a distal tip insertable into the proximal opening when the elongated inner catheter is inserted into the containing catheter and pressed into the distal stiff member.

Figure 1B:
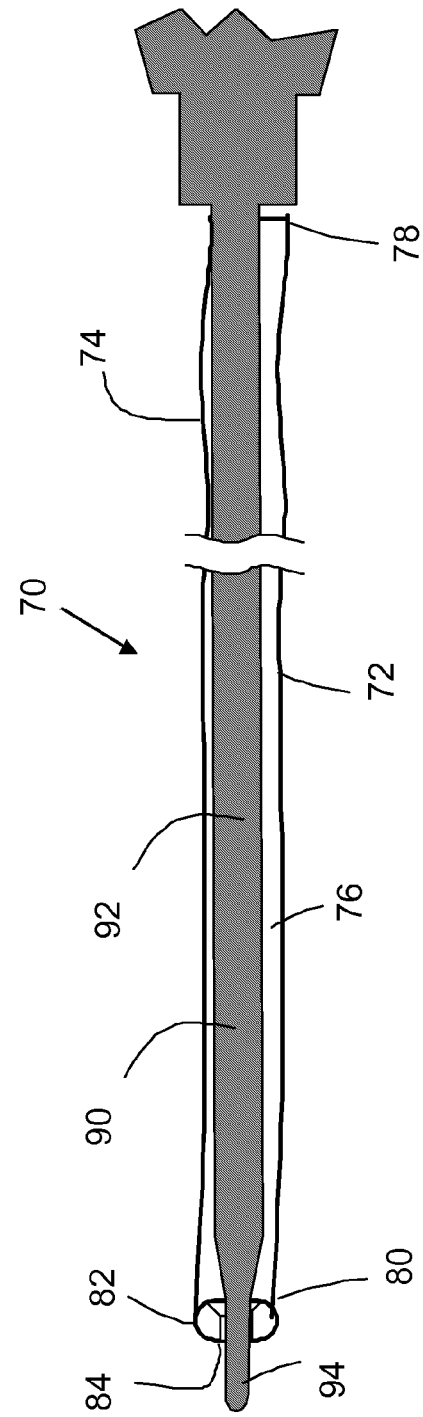
FIG. 1B schematically depicts a cross-sectional view of a catheterization apparatus comprising a containing catheter and an elongated inner catheter comprising a stiff and flexible portion that is insertable into the containing catheter.

According to some embodiments, a catheterization apparatus 70 (FIG. 1B) for facilitating sequential treatment operations, is provided. Catheterization apparatus 70 comprises a containing catheter 72 comprising a soft and elongated, substantially tubular member 74. The tubular member comprises a main lumen 76 therein, extending between a proximal end 78 and a distal end 80 of the tubular member, thereby providing fluid communication between the proximal end and the distal end of the tubular member. The containing catheter 72 further comprises a distal stiff member 82 coupled to the tubular member 74 at the distal end 80. Distal stiff member 82 comprises a proximal opening 84 facing tubular member 74 thereby having fluid communication with the main lumen 76.

Catheterization apparatus 70 further comprises an elongated inner catheter 90 insertable into containing catheter 72. Inner catheter 90 comprises a stiff and flexible portion 92, having a cross-section dimension similar to a cross section dimension of the main lumen 76. Flexible portion 92 further comprises a distal tip 94 insertable into the proximal opening 84 of containing catheter 72, when the elongated inner catheter 90 is inserted into the containing catheter 72 and pressed into the distal stiff member 82.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A catheterization apparatus comprising a containing catheter for facilitating sequential treatment operations and an elongated inner catheter, said containing catheter comprising:
   a median portion comprising an elongated, substantially tubular member, having a main lumen therein extending between a proximal end and a distal end of said tubular member, thereby providing fluid communication between said proximal end and said distal end of said tubular member;
   a distal portion, comprising a distal stiff member extending between a stiff member proximal end and a stiff member distal end, and comprising:
     a proximal opening located at said stiff member's proximal end, and comprising a mating surface of a sealed joint;
     a distal opening including an unobstructed open hole or an unobstructed open channel; and
     a stiff member void inside said stiff member, configured to provide fluid communication between said proximal opening and said distal opening;
   wherein said distal portion is physically associated with said median portion so that said stiff member void of said distal stiff member is in fluid communication with said main lumen,
   wherein said elongated inner catheter is insertable into said main lumen of said containing catheter, said elongated inner catheter has a cross-section dimension smaller than a cross-section dimension of said main lumen, thereby forming a gap between said inner catheter and an inner surface of said tubular member when said elongated inner catheter is inserted into said tubular member, said elongated inner catheter extends between an inner catheter proximal end and an inner catheter distal end, having a length greater than a length of said median portion of said containing catheter, and said elongated inner catheter has an inner catheter channel between a catheter proximal opening and a catheter distal opening, and
   wherein said elongated inner catheter distal end is blind and comprises an inner catheter mating surface configured to fit said mating surface of said proximal opening at said stiff member proximal end, and said distal catheter opening is proximal to said inner catheter distal end and facing said gap between said elongated inner catheter and said inner surface of said tubular member so that said sealing joint is formed between said inner catheter distal end and said proximal opening at said stiff member proximal end when said elongated inner catheter is inserted into said containing catheter and pressed onto said distal stiff member, said sealing joint prevents fluid flow through said proximal opening of said distal stiff member and fluid communication is provided between said inner catheter channel and said gap through said inner catheter distal opening.

2. The catheterization apparatus of claim 1 wherein said tubular member is stiff and flexible.

3. The catheterization apparatus of claim 1 further comprising a proximal portion comprising a rear connector having a front opening, a rear opening, a side opening and a connector void inside, said connector void providing fluid communication between said front opening, said rear opening and said side opening, and wherein said rear connector is physically associated with said proximal end of said tubular member thereby providing fluid communication between said main lumen and said connector void.

4. The catheterization apparatus of claim 3 further comprising at least one stiffening lumen extending at least along said tubular member of said median portion between a stiffening lumen proximal end and a stiffening lumen distal end, having a single stiffening lumen opening at said stiffening lumen proximal end allowing pressurized fluid into said stiffening lumen and thereby to stiffen said tubular member and hence to stiffen said median portion.

5. The catheterization apparatus of claim 3 wherein said connector void extends along a substantially straight line between said front opening and said rear opening thereby enabling insertion of a rigid elongated pole through said rear opening, said connector void and said front opening into said tubular member.

6. The catheterization apparatus of claim 1 wherein said distal stiff member is configured substantially as a cylinder having a cylinder side extending between said stiff member proximal end and said stiff member distal end.

7. The catheterization apparatus of claim 6 wherein said distal opening is located on said cylinder side.

8. The catheterization apparatus of claim 6 wherein said distal opening is located on said stiff member distal end.

9. The catheterization apparatus of claim 6 wherein said distal opening is configured as a guide wire channel thereby allowing insertion of said containing catheter into a body conduit guided along a guide wire passing through said stiff member void.

10. The catheterization apparatus of claim 9 further comprising a distal stiff member opening on said cylinder side of said distal stiff member, and wherein said stiff member void provides fluid communication between said proximal opening, said distal opening and said distal stiff member opening.

11. The catheterization apparatus of claim 1 further comprising:
- an inflatable balloon attached around an outer surface of said distal portion, and
- an inflating lumen extending at least along said median portion between an inflating lumen proximal opening and an inflating lumen distal opening, said inflating lumen distal opening being located inside said inflatable balloon,
- wherein said inflatable balloon can be inflated and deflated through said inflating lumen between a relaxed state, having a first outer radius and an inflated state having a second outer radius larger than said first outer radius.

12. The catheterization apparatus of claim 1 wherein said elongated inner catheter comprises a stiff and flexible portion, enabling stiffening of said tubular member when inserted therein and allowing for inserting such stiffened containing catheter into a body conduit.

13. The catheterization apparatus of claim 1 wherein said elongated inner catheter is displaceable inside said containing catheter and the catheterization apparatus has at least two operational states according to an arrangement of said elongated inner catheter inside said containing catheter, wherein:
- in a first operational state said elongated inner catheter is advanced until said inner catheter distal end is pressed onto said mating surface of said proximal opening of said distal stiff member, so that a fluid forced into said inner catheter hollow channel flows towards said inner catheter distal end inside said inner catheter hollow channel, exits said inner catheter hollow channel through said distal catheter opening, and flows in said gap inside said main lumen towards said proximal end, while fluid flow through said proximal opening of said distal stiff member is prevented, and
- in a second operational state said elongated inner catheter is retreated inside said containing catheter so that said inner catheter distal end disengages from said mating surface of said proximal opening of said distal stiff member thereby allowing fluid flow through said distal opening and between said stiff member void and said main lumen of said containing catheter through said proximal opening.

14. The catheterization apparatus of claim 1 wherein said elongated inner catheter comprises a rigid pole insertable into said containing catheter, and extends between said inner catheter distal end to a length greater than said median portion of said containing catheter.

15. The catheterization apparatus of claim 14 further comprising an external handle fixedly attached to said inner catheter allowing a user to manipulate said inner catheter during insertion into said containing catheter inside a body conduit.

16. The catheterization apparatus of claim 14 further comprising:
- a mechanical arm mechanically attached to said elongated inner catheter proximal to said inner catheter proximal end; and
- a positioning template mechanically attached to said mechanical arm and configured to fixedly attach to a treatment tool,
- wherein position and orientation of said positioning template relative to said rigid pole can be established by a user by controllably modifying at least one of said mechanical attachments, thereby allowing aiming a treatment tool attached to said positioning template to a treatment locus having a known spatial relationship with said rigid pole.

17. A method of catheterization, comprising:
providing the catheterization apparatus of claim 1;
stiffening the median portion of the containing catheter;
inserting the stiffened containing catheter into a body conduit of a patient;
inserting the elongated inner catheter into the containing catheter and pressing the second inner catheter onto the distal stiff member, thereby preventing fluid flow through the proximal opening of the distal stiff member;
forcing a fluid into one of the inner catheter channel and the main lumen, and
collecting the forced fluid from the other of the inner catheter channel and the main lumen.

18. The method of claim 17 further comprising:
retreating the elongated inner catheter inside the containing catheter so that the inner catheter distal end disengages from the mating surface of the proximal opening of the distal stiff member, thereby allowing fluid communication between the stiff member void and the main lumen of the containing catheter through the proximal opening.

* * * * *